United States Patent [19]

McMillan et al.

[11] 4,360,531

[45] Nov. 23, 1982

[54] SUBSTITUTED CYCLOALKANES

[75] Inventors: Moses W. McMillan, Portage; Jacob Szmuszkovicz, Kalamazoo, both of Mich.

[73] Assignee: The Upjohn Company, Kalamazoo, Mich.

[21] Appl. No.: 252,535

[22] Filed: Apr. 9, 1981

[51] Int. Cl.$^3$ .................... C07D 487/00; A61K 31/40
[52] U.S. Cl. .................................... 424/274; 548/407; 549/39; 549/333; 260/239 A; 260/465 E; 546/15; 546/230; 546/231; 546/234; 560/16; 560/251; 564/155; 564/162; 564/163; 564/166; 424/304; 424/309; 424/244; 424/311; 424/324; 424/267; 424/275; 424/278
[58] Field of Search ........... 260/326.4, 326.35, 326.36, 260/239 A, 340.9 R, 465 E; 424/274, 244, 267, 275, 278, 304, 309, 311, 324; 564/155, 162, 163, 166; 546/15, 230, 231, 234; 560/16, 251; 549/39

[56] References Cited

U.S. PATENT DOCUMENTS

| | | | |
|---|---|---|---|
| 3,510,492 | 5/1970 | Szmuszkovicz | 546/232 |
| 4,065,573 | 12/1977 | Lednicer | 424/278 |
| 4,098,904 | 7/1978 | Szmuszkovicz | 424/324 |
| 4,145,435 | 3/1979 | Szmuskovicz | 424/274 |
| 4,156,733 | 5/1979 | Szmuszkovicz | 260/326.4 |
| 4,212,878 | 7/1980 | Lednicer et al. | 424/274 |

*Primary Examiner*—Jane T. Fan
*Attorney, Agent, or Firm*—John T. Reynolds

[57] ABSTRACT

[2-Amino(substituted cycloaliphatic)]benzeneacetamide and benzamide compounds, e.g., trans-3,4-dichloro-N-methyl-N-[7-(1-pyrrolidinyl)-1,4-dioxaspiro[4.5]dec-8-yl]benzeneacetamide, have useful analgesic activity and low abuse or physical dependence liability, or are useful as chemical intermediates for producing such analgesic compounds. Processes for their preparation are disclosed. Pharmaceutical compositions and methods of use are also disclosed.

26 Claims, No Drawings

SUBSTITUTED CYCLOALKANES

DESCRIPTION

INTRODUCTION

This invention relates to N-[2-amino(oxy-group-substituted-cycloaliphatic)]phenylacetamide and -benzamide compounds. More particularly, this invention provides some new N-[(2-amino-(oxy-group-substituted-cycloaliphatic)]phenylacetamide and -benzamide compounds which have useful analgesic activity and low abuse liability, or which are useful as chemical intermediates to such useful compounds. Processes for their preparation are disclosed. Pharmaceutical compositions and methods of use are also provided.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[2-(N',N'dimethylamino)cyclohexyl]-N-methyl-2-(4-bromophenyl)-acetamide and trans-N-methyl-N-[2-(1-pyrrolidinyl)cyclohexyl]-2-(3,4-dichlorophenyl)acetamide, which have potent analgesic activity; the preferred compounds thereof have, in addition, only low to moderate apparent physical dependence liability compared to morphine and methadone. That Szmuszkovicz '435 patent also describes some prior art patent and publication background that may be of interest herein also.

Also, Szmuszkovicz U.S. Pat. No. 4,098,904 discloses some cis- and trans-N-(2-aminocycloaliphatic)benzamide compounds, e.g., N-methyl-N-[2-aminocycloaliphatic]benzamide compounds, e.g., N-methyl-N-[2-(1-pyrrolidinyl)cyclohexyl]-3,4-dichlorobenzamide, which have potent analgesic activity, making them useful for relieving pain in warm blooded animals. That '904 patent also discloses background patents and publications which may be of interest herein.

Lednicer U.S. Pat. No. 4,212,878, discloses some N-[(1-amino-4-(mono- or di-oxygen-group-substituted)-cyclohexyl)methyl]benzeneacetamide derivatives, e.g., 2-(3,4-dichlorophenyl)-N-[[8-(1-pyrrolidinyl)-1,4-dioxaspiro[4.5]dec-8-yl]-methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclo-hexanone ketal compounds, e.g., 4-(m-hydroxyphenyl)-4-(dimethylamino)-cyclohexanone ethylene ketal and 4-(m-hydroxyphenyl)-4-(n-butylmethyl-amino)cyclohexanone ethylene ketal, which are useful for relieving pain in animals, some of which compounds exhibit narcotic antagonist ractivity.

Other references are listed in the accompanying prior art statement.

Representative compounds of some of the above types have been or are being studied in advanced animal drug studies. Some concern has been expressed about possible dysphoric side effects of such compounds when used as analgesic drugs. Those skilled in the art continue to search for new and more advantageous analgesic compounds.

OBJECTS OF THE INVENTION

It is an object of the invention to provide some new N-[(oxy or thio group substituted)-2-aminocycloaliphatic]benzeneacetamide and -benzamide compounds which are useful as analgesic compounds or as chemical intermediates to analgesic compounds.

It is a further object of this invention to provide some new compounds of the above type which have useful analgesic properties, only low to moderate physical dependence liability compared to the high physical dependence liability of morphine and methadone and, hopefully also, less dysphoria inducing properties than prior known analgesic compounds.

Other objects, aspects, and advantages of this invention will become apparent from reading the remaining specification and claims which follow.

SUMMARY OF THE INVENTION

Briefly, this invention provides some new 2-aminocycloaliphatic-benzeneacetamide and -benzamide compounds bearing oxy- or thio group substituents on a cycloaliphatic ring carbon not adjacent to the nitrogen bearing carbons of that cycloaliphatic ring, e.g., trans3,4-dichloro-N-methyl-N-[7-(1-pyrrolidinyl)-1,4-dioxaspiro[4.5]-dec-8-yl]benzeneacetamide, and salts thereof, which have been found to have useful ranges of analgesic properties while also having low apparent physical dependence liability, and which also, hopefully, have reduced dysphoria inducing properties. This invention also includes compounds of the above general type which may exhibit some analgesic activity of their own, but which are of more importance as chemical intermediates for the preparation of more advantageous analgesic drug compounds included herein. This invention also includes pharmaceutical compositions containing these compounds as an active analgesic component and the method of inducing analgesic activity in an animal patient, including humans, by administering one of these new compounds in an amount effective and sufficient to induce analgesic activity, regardless of origin, e.g., traumatic pain, bone pain, cancer pain, post-surgical pain, homotopic pain, menstrual pain, headache, and the like. The invention also relates to new compounds in pharmaceutical dosage unit forms to be used, hopefully more advantageously, for the relief of pain in valuable animals and human patients suffering pain.

DETAILED DESCRIPTION OF THE INVENTION

More particularly, this invention provides some new compounds having a chemical structure of Formula I below wherein p and n are each integers independently selected from the group 1, 2 and 3 so that the resulting cycloaliphatic ring of Formula I has from 5 to 7 ring carbon atoms, inclusive, and the $R_3$ and $R_4$ bearing carbon is separated from the nitrogen bearing carbons of that cycloaliphatic ring by at least one ring methylene group.

In detail, the compounds of this invention are those of the formula

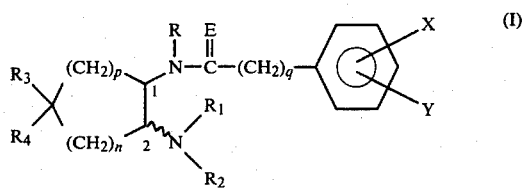

wherein p and n are each full number integers of from 1 to 3, so that the resulting cycloaliphatic ring has five to seven carbon atoms; the wavy line bond (~) between the nitrogen in the 2-position and the cycloaliphatic ring carbon indicates the bond can be either cis- or trans- with respect to each substituent of the cycloaliphatic ring;

q is 0 or 1;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino [(—NHC(O)$R_6$)];

R is hydrogen or $C_1$ to $C_3$-alkyl;

$R_1$ and $R_2$, taken separately, are hydrogen, $C_1$ to $C_3$-alkyl, allyl, or $R_1$ and $R_2$ taken together with the nitrogen to which they are bonded, complete a ring selected from the group consisting of azetidinyl, pyrrolidinyl and piperidinyl;

$R_3$, taken separately, is hydrogen, hydroxy, —O$R_5$ or OC(=O)$R_6$;

$R_4$, taken separately, is hydrogen;

$R_3$ and $R_4$, taken together, are selected from the group consisting of

—ECH$_2$CH$_2$E—,

=E,

=N~OH, and

=N~OC(O)CH$_3$, wherein each E is bivalent sulfur or oxygen, and $R_3$ and $R_4$ cannot both be hydrogen at the same time;

$R_5$ is $C_1$ to $C_3$-alkyl;

$R_6$ is H, or $C_1$ to $C_2$-alkyl; and the acid addition salts thereof, particularly pharmaceutically acceptable salts thereof, provided that when R is methyl, $R_1$ and $R_2$ taken together with the nitrogen to which they are bonded form a pyrrolidinyl, X and Y are each chlorine in the 3- and 4-positions of the phenyl ring, p is 1, n is 2, q is 1, E is oxygen, $R_4$ is hydrogen, then $R_3$ cannot be acetoxy with a 5-alpha orientation (on the same side of the cycloaliphatic ring as the amide nitrogen). Thus the $R_3$, $R_4$ substituent moiety is in the 4- position of cyclopentyl ring compounds, in the 4- or 5-position of cyclohexyl ring compounds (or a mixture of compounds wherein the $R_3$ and $R_4$ substituents are on the 4- and 5- positions), and in the 4-, 5- or 6-positions of cycloheptyl ring compounds (or a mixture of such $R_3$, $R_4$ position isomers). Thus, this invention involves compounds wherein the $R_3$, $R_4$ bearing carbon is not vicinal (adjacent) to either of the nitrogen bearing carbons of that same cycloaliphatic ring.

The compounds of formula (I) or their acid addition salts in their crystalline state may sometimes be isolated from their reaction mixtures as solvates, i.e., with a discrete quantity of solvent, e.g., water, ethyl acetate, methanol, and the like, associated physically, and thus not affecting the chemical entity per se.

It will be recognized by those skilled in the organic chemical art that the carbon atoms at positions 1 and 2 of the cycloaliphatic ring of structure (I) to which nitrogens are bonded are asymmetrically substituted. Likewise, for certain definitions of $R_3$ and $R_4$, the cycloaliphatic ring carbon atom to which $R_3$ and $R_4$ are bonded may also be asymmetrically substituted. Each of these three carbon atoms can independently possess an R or S- configuration and thus a compound of the formula (I) may have as many as $2^3$ or 8 stereoisomers which comprise four pairs of enantiomers; each enantiomeric pair is termed a racemate. See, for example J. B. Hendrickson, D. J. Cram, and G. S. Hammond, Organic Chemistry, Third Edition, McGraw-Hill Book Company, New York, N.Y. 1970, pages 198–230, particularly pages 207, 208, 213, 215. Of the four racemates, two will have the nitrogen-containing groups at positions 1 and 2 of structure (I) in a trans orientation: that is, the groups will be on opposite sides of the plane of the cycloaliphatic ring; such compounds will be generally referred to in this specification as trans compounds and are meant to include both possible configurations of the third ring carbon if it is asymmetrically substituted. The other two racemates will have the nitrogen-containing groups at positions 1 and 2 of structure (I) in a cis orientation: that is, the groups will be on the same side of the cycloaliphatic ring; such compounds will be generally referred to in this specification as cis compounds and are meant to include both possible configurations of the third substituted ring carbon atom if it is asymmetrically substituted. The four racemates of structure (I) compounds can each exist as a mixture of the two enantiomers or each enantiomer of each pair can be separated. When it is desired to specify for a structure (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972-1976)," a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of formula I compounds is indicated by: (1) the arbitrary designation of $1\alpha$ for the orientation of the substituent on (asymmetric) carbon atom number one; (2) the designation $2\alpha$ or $2\beta$ when the substituent on (asymmetric) carbon atom number two is on the same or opposite side of the plane of the cycloaliphatic ring, respectively, relative to said $C_1$ substituent; and (3) the designation $x\alpha$ or $x\beta$ when the substituent on (asymmetric) carbon atom number x is on the same or opposite side of the plane of the cycloaliphatic ring, respectively, relative to said $C_1$ substituent.

Two isomers which differ only in the stereochemistry at one asymmetric carbon atom of the cyloaliphatic ring are referred to as epimers.

In the above Formula I compounds, the halogens having atomic numbers of from 9 to 35 are fluorine, chlorine and bromine, the term "$C_1$ to $C_3$-alkyl" means methyl, ethyl, n-propyl and isopropyl.

A preferred subgroup of these Formula I compounds are those wherein p is 1 to 3, n is 1 to 3 and p and n are selected so that the cycloaliphatic ring has 5 to 7 ring carbons, q is 0 or 1, and at least one of X and Y is a halogen having an atomic number of from 9 to 35 in the 3- or 4- positions, or both of X and Y are such halogens in the 3- and 4-positions of the phenyl ring;

R is $C_1$ to $C_3$-alkyl;

$R_1$ and $R_2$ are taken together with the nitrogen to which they are bonded to complete an azetidinyl, pyrrolidinyl or piperidinyl ring;

$R_3$ and $R_4$ are taken together to form the ring group —ECH$_2$CH$_2$E— and each E is oxygen, and the pharmacologically acceptable salts thereof. Examples of compounds of this group include the cis- and trans- isomers of:

3,4-dichloro-N-methyl-N-[8-(1-pyrrolidinyl)-1,4-dioxaspiro[4.5]-dec-7-yl]-benzeneacetamide, 3,4-dichloro-N-methyl-N-[7-(1-pyrrolidinyl)-1,4-dioxaspiro[4.5]-dec-8-yl]-benzeneacetamide, 4-bromo-N-methyl-N-[7-(1-pyrrolidinyl)-1,4-dioxaspiro[4.5]dec-8-yl]benzeneacetamide, 3-fluoro-N-ethyl-N-[7-(1-azetidinyl)-1,4-dioxapiro[4.5]dec-8-yl]benzeneacetamide, 3,4-dibromo-N-propyl-N-[7-(1-piperidinyl)-1,4-dioxaspiro[4.5]dec-8-yl]benzeneacetamide, 3,4-dichloro-N-methyl-N-[7-(1-pyrrolidinyl)-1,4-dioxaspiro[4.4]-non-8-yl]-benzeneacetamide, 3,4-dichloro-N-methyl-N-[7-(1-pyrrolidinyl)-1,4-dioxaspiro[4.6]-undec-8-yl]-benzeneacetamide, 3,4-dichloro-N-methyl-N-[8-(1-pyrrolidinyl)-1,4-dioxaspiro[4.6]-undec-7-yl]-benzeneacetamide, 3,4-dichloro-N-methyl-N-[9-(1-pyrrolidinyl)-1,4-dioxaspiro[4.6]-undec-8-yl]-benzeneacetamide, and the corresponding benzamides, e.g., 4-bromo-N-methyl-N-[7-(1-pyrrolidinyl)-1,4-dioxaspiro[4.5]dec-8-yl]benzamide, 3,4-dichloro-N-methyl-N-[7-(1-azetidinyl)-1,4-dioxaspiro[4.5]dec-8-yl]-benzamide, 3,4-dichloro-N-methyl-N-[7-(1-pyrrolidinyl)-1,4-dioxaspiro[4.4]-non-8-yl]-benzamide, 3,4-dichloro-N-methyl-N-[7-(1-pyrrolidinyl)-1,4-dioxaspiro[4.6]-undec-8-yl]-benzamide, 3,4-dichloro-N-methyl-N-[8-(1-pyrrolidinyl)-1,4-dioxaspiro[4.6]-undec-7-yl]-benzamide, 3,4-dichloro-N-methyl-N-[9-(1-pyrrolidinyl)-1,4-dioxaspiro[4.6]-undec-8-yl]-benzamide, and the like, and the pharmacologically acceptable salts thereof.

Another preferred group of compounds of Formula I are those wherein p is 1 to 3, n is 1 to 3, such that the cycloaliphatic ring has from 5 to 7 ring carbon atoms; q is 0 or 1; at least one of X and Y is a halogen having an atomic number of from 9 to 35 in the 3- or 4- position or both of X and Y are such halogens in the 3- and 4- positions of the phenyl ring; R is $C_1$ to $C_3$-alkyl; $R_1$ and $R_2$ are taken together with the nitrogen to which they are bonded to complete an azetidinyl, pyrrolidinyl or piperidinyl ring; one of $R_3$ and $R_4$ is hydrogen and the other of $R_3$ and $R_4$ is methoxy; and the pharmacologically acceptable salts thereof. Examples of such compounds include the cis- and trans- isomers of 4-bromo-N-[5-methoxy-2-(1-pyrrolidinyl)cyclohexyl]-N-methylbenzamide, 3,4-dichloro-N-[4-methoxy-2-(1-pyrrolidinyl)cyclohexyl]-N-methylbenzeneacetamide, 3,4-difluoro-N-[4-methoxy-2-(1-piperidinyl)cyclohexyl]-N-ethylbenzamide, 3,4-dibromo-N-[5-methoxy-2-(1-azetidinyl)cyclohexyl]-N-methylbenzeneacetamide, 3,4-dichloro-N-[4-methoxy-2-(1-pyrrolidinyl)cyclopentyl]-N-methylbenzeneacetamide, 3,4-dichloro-N-[4-methoxy-2-(1-pyrrolidinyl)cycloheptyl]-N-methylbenzamide, 3,4-dichloro-N-[5-methoxy-2-(1-pyrrolidinyl)cycloheptyl]-N-methylbenzeneacetamide 3,4-dichloro-N-[6-methoxy-2-(1-pyrrolidinyl)cycloheptyl]-N-methylbenzamide, and the pharmacologically acceptable salts thereof.

Examples of other preferred compounds within the scope of this invention include:

(a) compounds of Formula I wherein p is 1 to 3, n is 1 to 3, such that the cycloaliphatic ring has 5 to 7 carbon atoms therein; q is 0 or 1; at least one of X and Y is a halogen having an atomic number of from 9 to 35 in the 3-, or 4- positions, or both of X and Y are such halogens in the 3- and 4- positions of the phenyl ring; R is hydrogen or $C_1$ to $C_3$-alkyl; $R_1$ and $R_2$ are each independently hydrogen, $C_1$ to $C_3$-alkyl, or are taken together with the nitrogen to which they are bonded to complete an azetidinyl, pyrrolidinyl or piperidinyl ring; $R_3$ and $R_4$ are taken together to represent =E; E is oxygen and the pharmacologically acceptable salts thereof, examples of which are the cis- and trans- isomers of 3,4-dichloro-N-methyl-N-[4-oxo-2-(1-pyrrolidinyl)-cyclohexyl]-benzeneacetamide, 4-bromo-N-methyl-N-[4-oxo-2-(1-piperidinyl)cyclohexyl]benzamide, 3,4-difluoro-N-ethyl-N-[2-(1-azetidinyl)-4-oxo-cyclohexyl]benzeneacetamide, 3,4-dichloro-N-propyl-N-[5-oxo-2-(1-piperidinyl)cyclohexyl]-benzamide, 4-bromo-N-methyl-N-[2-(N',N'-dimethylamino)-4-oxo-cyclohexyl]benzeneacetamide, 3,4-dichloro-N-methyl-N-[4-oxo-2-(1-pyrrolidinyl)-cyclopentyl]-benzamide, 3,4-dichloro-N-methyl-N-[4-oxo-2-(1-pyrrolidinyl)-cycloheptyl]-benzeneacetamide, 3,4-dichloro-N-methyl-N-[5-oxo-2-(1-pyrrolidinyl)-cycloheptyl]-benzamide, 3,4-dichloro-N-methyl-N-[6-oxo-2-(1-pyrrolidinyl)-cycloheptyl]-benzeneacetamide and the like, and the pharmacologically acceptable salts thereof.

(b) compounds of Formula I wherein p is 1 to 3, n is 1 to 3, such that the cycloaliphatic ring has 5 to 7 carbon atoms; q is 0 or 1; at least one of X and Y is a halogen having an atomic number of from 9 to 35 in the 3- or 4-positions, or both X and Y are such halogens in the 3- and 4- positions of the phenyl ring; R is hydrogen or $C_1$ to $C_3$-alkyl; each of $R_1$ and $R_2$ is independently hydrogen, $C_1$ to $C_3$-alkyl, or $R_1$ and $R_2$ are taken together with the nitrogen to which they are bonded to complete an azetidinyl, pyrrolidinyl, or piperidinyl ring; one of $R_3$ and $R_4$ is hydrogen and one of $R_3$ and $R_4$ is acetoxy; and the pharmacologically acceptable salts thereof, examples of which are the cis- and trans- isomers of N-[4-acetyloxy-2-(1-pyrrolidinyl)cyclohexyl]-3,4-dichloro-N-methylbenzeneacetamide, N-[5-acetyloxy-2-(dimethylamino)cyclohexyl]-4-bromo-N-methylbenzamide, N-[4-acetyloxy-2-aminocyclohexyl]-3,4-difluoro-N-ethylbenzeneacetamide, N-[4-acetyloxy-2-(methylamino)cyclohexyl]-3,4-dibromo-N-(n-propyl)benzamide, N-[4-acetyloxy-2-(1-pyrrolidinyl)cyclopentyl]-3,4-dichloro-N-methylbenzeneacetamide, N-[4-acetyloxy-2-(1-pyrrolidinyl)cycloheptyl]-3,4-dichloro-N-methylbenzamide, N-[5-acetyloxy-2-(1-pyrrolidinyl)cycloheptyl]-3,4-dichloro-N-methylbenzeneacetamide, N-[6-acetyloxy-2-(1-pyrrolidinyl)cycloheptyl]-3,4-dichloro-N-methylbenzamide, and the like, and the pharmacologically acceptable salts thereof.

In general, and with the exceptions set forth below, the new compounds of this invention (Formula I compounds above) can be prepared by reacting the selected 1,2-cycloaliphatic diamine of the formula II,

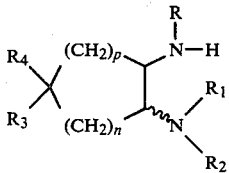

wherein p, n, R, $R_1$, $R_2$, $R_3$, and $R_4$ are as defined above with: (1) a suitable acyl source such as the appropriate acyl imidazole of the formula

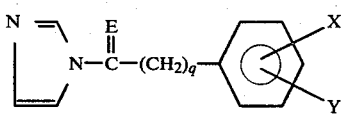

wherein q, E, X and Y are as defined above; (2) or with an acyl halide of the formula

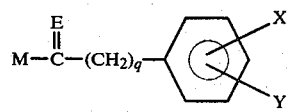

wherein M is chloride or bromide and q, E, X and Y are as defined above in the presence of an acid scavenger such as triethylamine; or (3) with the carboxylic acid of the formula

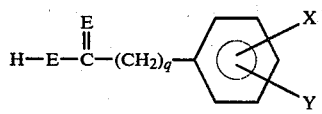

in the presence of a condensing agent, such as a carbodiimide, wherein q, E, X and Y are as defined above, in an organic solvent for the reactants, preferably in an ether solvent such as diethyl ether, or a cyclic ether solvent such as tetrahydrofuran (THF) or dioxane, or the like, until the compound of this invention is produced. Carbodiimides such as dicyclohexylcarbodiimide or diisopropylcarbodiimide can be used.

The reactants (II) and (III) or (II) and (IV) or (II) and (V) can be mixed in substantially equimolar proportions to effect formation of the desired product (I), but in cases where the non-pertinent amino nitrogens are protected against reaction, if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process.

Exceptions—When the new compound of this invention is to be one of formula (I) in which one or both of $R_1$ and $R_2$ is to be hydrogen, the amino-hydrogens in the $R_1$ and/or $R_2$ positions must first be protected by procedures known in the art, then the N-protected diamine reactant (IIa)

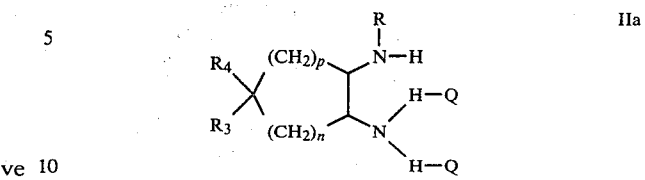

wherein R, $R_3$, $R_4$, n and p are as defined for formula II and each "—H—Q" denotes a protected amino hydrogen group, reacted with the selected acyl imidazole (III), or with the acyl halide (IV) or with the carboxylic acid (V) in the presence of a condensing agent, to form the N-[2-(N-protected-amino)oxy or thio- group-substituted cycloaliphatic]benzamide or -phenylacetamide, which is then treated to remove the N-protecting group to leave as product the desired N-[2-(amino)oxy or thio-group-substituted-cycloaliphatic]benzamide or -phenylacetamide.

Procedures for preparing the aracyl imidazoles (II) and acyl halide (IV) reactants used to form compounds of this invention are known in the art. See, for example, R. B. Wagner and H. D. Zook, *SYNTHETIC ORGANIC CHEMISTRY*, 1953, John Wiley and Sons, Chapter 17, p. 546 et seq. The aracyl imidazole can be prepared in situ by reacting carbonyldiimidazole with the acid of the formula (V) in an organic solvent. The carboxylic acids V are either known in the art or are prepared by methods known in the art.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, furmaric, oxalic acids and the like. The reaction can be carried out in aqueous or organic liquid solvent or non-aqueous media such as diethyl ether, ethyl acetate, and the like. Non-aqueous media are preferred. When it is desired to obtain optically resolved products in crystalline from, it may be more convenient to form salts such as maleates, citrates or pamoates rather than inorganic acid addition salts, such as the hydrochlorides. Also, whereas oxalic acid and other equivalent acids can be used to produce the amino-amide product in a more easily handled solid form, e.g., in plant manufacturing isolation procedures, it would preferably not be used as a pharmaceutically acceptable salt form of the amino-amide product.

Procedures for preparing the oxy-group substituted diamines (II) useful for preparing the compounds of this invention can be summarized by the following chemical reaction Charts.

The processes used to make compounds of this invention are illustrated in Charts A, B, C, and D. In these Charts R, $R_1$, $R_2$, $R_5$, $R_6$, p, n, q, E, X, and Y are as defined above; B is as defined in Chart A. The products of these reactions can be isolated and purified by conventional means. In the formulas (XVIII), (XIX) and (XX), the wavy line bond ($\sim$) between an oxygen atom and a carbon atom of the cycloalkyl ring can be either a solid-line bond ( — ) (up or above the plane of the ring) or a dashed-line bond ( --- ) (down or below the plane of the ring), and thus each of these formulas can represent a mixture of the two oxygen-group epimers or one or the other single epimer of unspecified stereochemistry.

In Charts A, B, C, and D, R' is R or a suitable nitrogen protecting group; R'$_1$ is R$_1$ or a suitable nitrogen protecting group; R'$_2$ is R$_2$ or a suitable nitrogen protecting group; R$_7$ is hydrogen or a suitable nitrogen protecting group. Examples of suitable nitrogen protecting groups are: (1) benzyl (C$_6$H$_5$—CH$_2$—); (2) triphenylmethyl (trityl, (C$_6$H$_5$)$_3$C); (3) para-toluenesulfonyl (p—CH$_3$—C$_6$H$_4$—SO$_2$—); and (4) trialkylsilyl, for example, trimethylsilyl ((CH$_3$)$_3$Si—) or tertiary butyldimethylsilyl ((CH$_3$)$_3$CSi(CH$_3$)$_2$—); (5) tert-butyloxycarbonyl and the like. Introduction and removal of such nitrogen protecting groups are well known in the art of organic chemistry: see, for example, (1) J. F. W. McOmie, Advances in Organic Chemistry, Vol. 3, pages 191-281 (1963); (2) R. A. Boissonas, Advances in Organic Chemistry, Vol. 3, pgs. 159-190 (1963); (3) "Protective Groups in Organic Chemistry," J. F. W. McOmie, ed., Plenum Press, New York, 1973, pg. 74.

The requisite hydroxycycloalkanones of the formula (VI) in Chart A are known in the art are thus suitable starting materials for the process outlined in Chart A. In addition some of the keto ketals of the formula (VIII) and some of the hydroxy ketals of the formula (VII) are known in the art; those which are not known are prepared from compounds of the formula (VI) by well known methods. The amines of the formulas R'NHR$_7$ and HNR'$_1$R'$_2$ are either known in the art or prepared by standard methods.

Under certain circumstances it is necessary to protect two different nitrogens with different protecting groups such that one such protecting group can be selectively removed while leaving the second protecting group in place. The trityl and benzyl protecting groups can be used in this way, the trityl group being removable in the presence of the benzyl group under acidic conditions. Likewise, the tert-butyloxycarbonyl and benzyl groups can be used in this way.

The requirements for protective groups in Charts A, B, C, and D are generally well recognized by one skilled in the art of organic chemical synthesis, and the use, when required, of the appropriate protecting group or groups is indicated in the Charts A, B, C, and D by the use of the symbols R', R'$_1$, R'$_2$, and R$_7$; removal of a protecting group is implied when R', R'$_1$, R'$_2$ or R$_7$ is replaced in a subsequent formula by R, R$_1$, R$_2$, or H, respectively; N-protected compounds can be deprotected as desired by known methods.

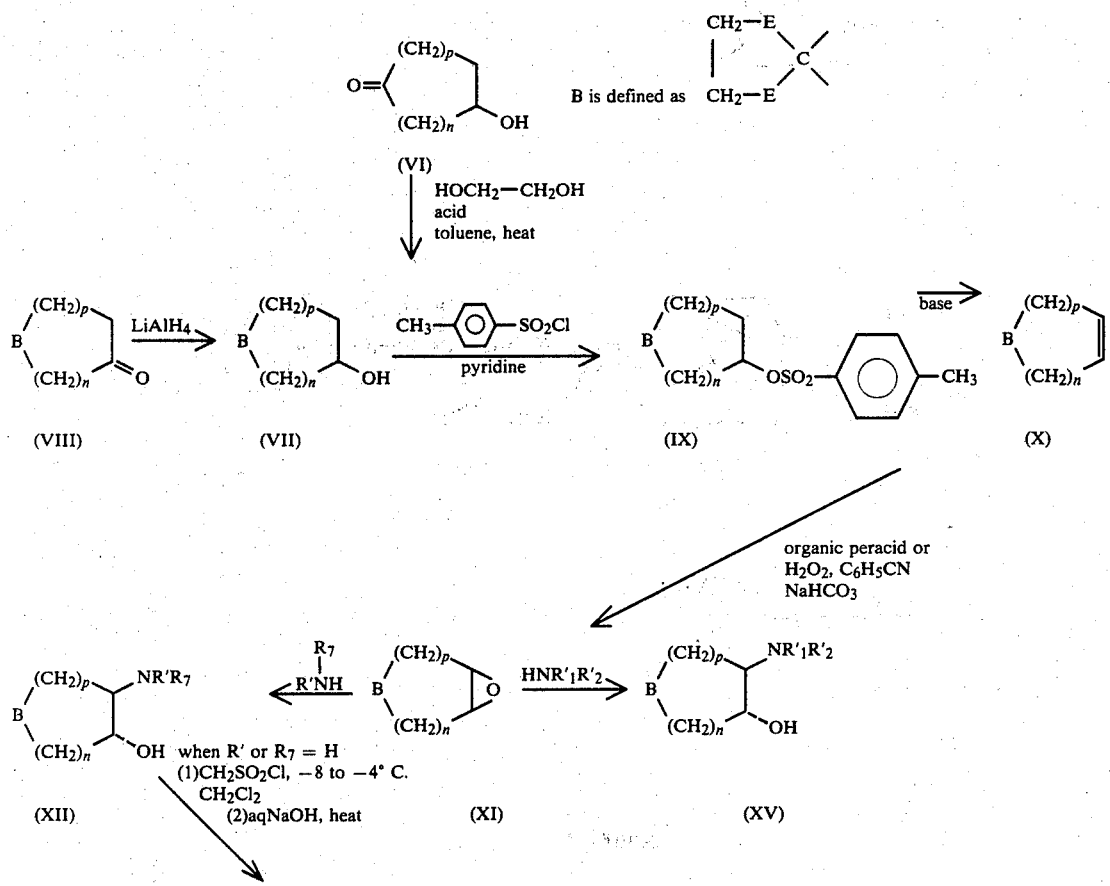

CHART A

-continued
CHART A
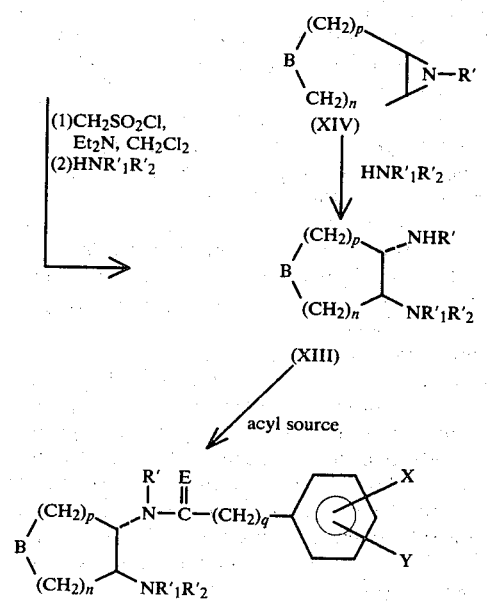
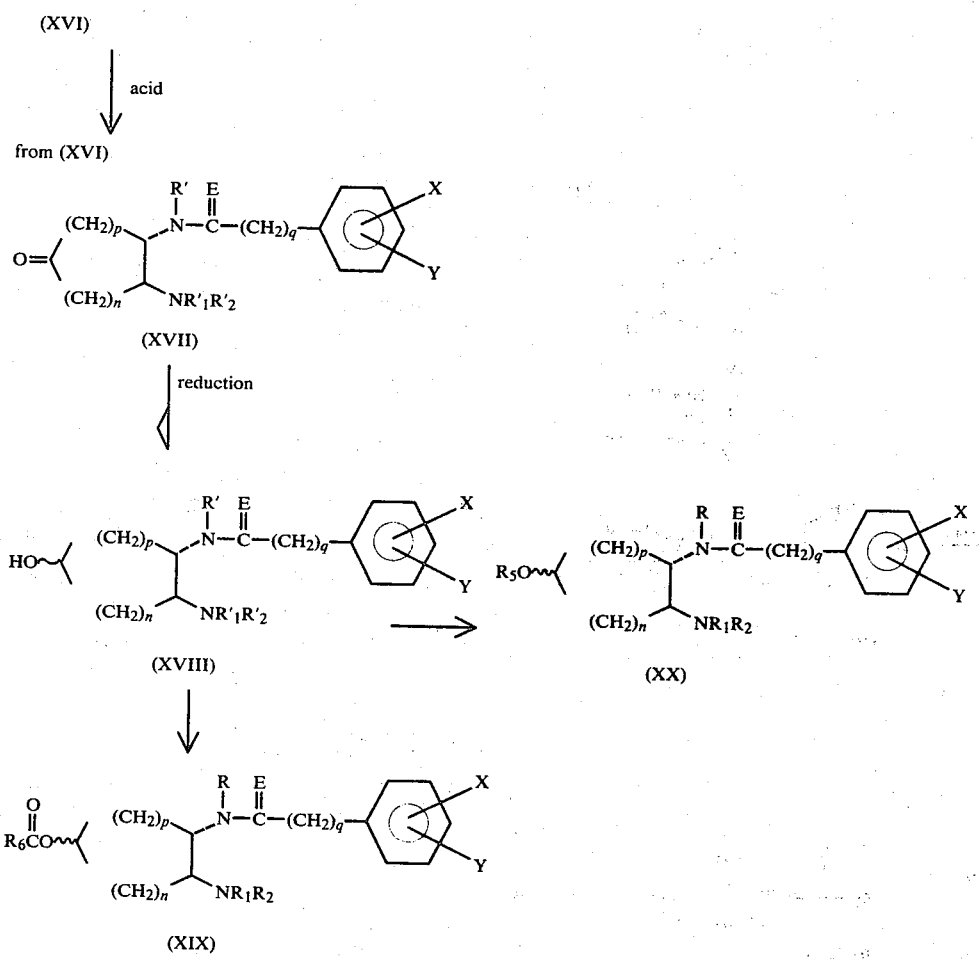
CHART B

-continued
CHART B

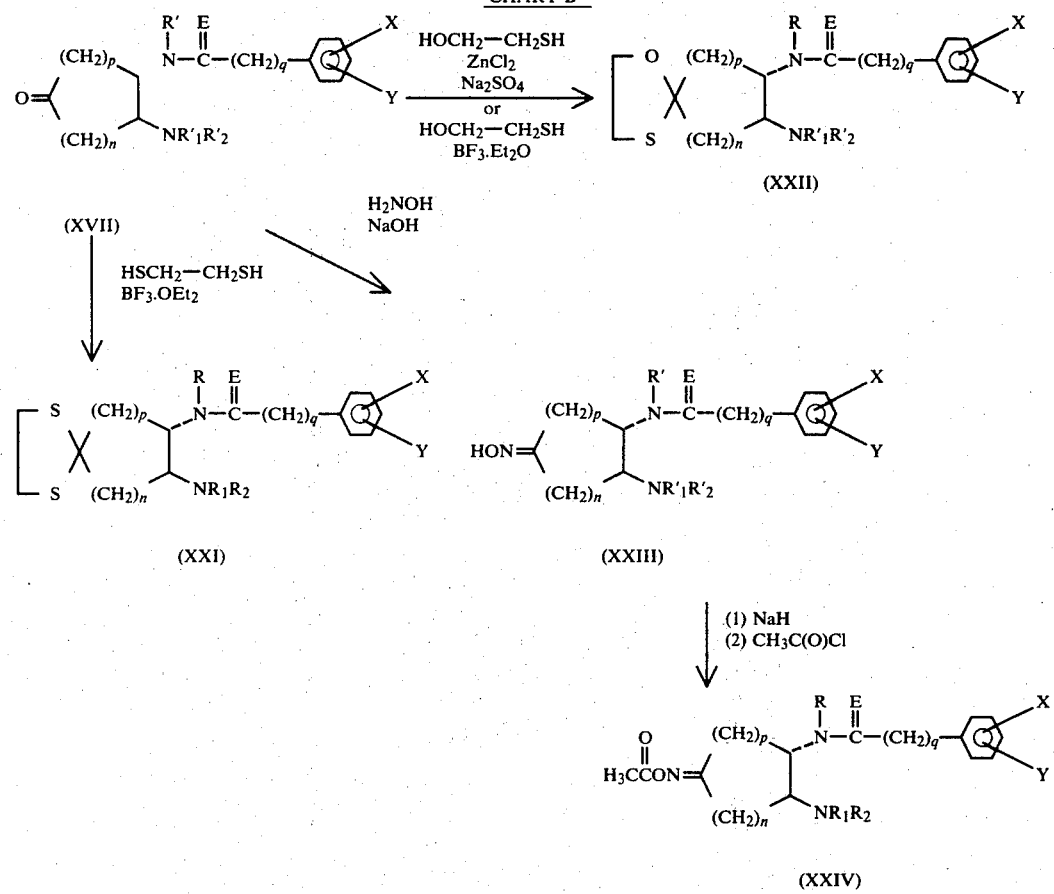

Introduction of the amino protecting groups is preferably accomplished by using suitable protected amino starting materials. The choice of protecting groups should be made such that the groups X and Y are not undesirably altered by the conditions for introduction or removal of these protecting groups.

The volatility of one or more reactants may require the use of a closed reaction vessel for some of the reactions described below.

Compounds of this invention of the formulas (XVI), (XVII), (XVIII) (XIX) and (XX) are prepared using the process steps illustrated in Chart A. A suitable keto alcohol of the formula (VI) is reacted with an appropriate glycol and a catalytic amount of an acid such as p-toluenesulfonic acid with azeotropic removal of water to afford a hydroxy ketal of the formula (VII). Alternatively, reduction of a suitable compound of the formula (VIII) with a suitable reducing agent such as lithium aluminum hydride in a suitable solvent such as diethyl ether or tetrahydrofuran gives a hydroxy ketal of the formula (VII). Reaction of a hydroxy ketal compound of the formula (VII) with p-toluenesulfonyl chloride in pyridine yields a sulfonate ester of the formula (IX), which sulfonate ester is reacted with a suitable base such as 1,5-diazabicyclo[4.3.0]non-5-ene (DBN) to produce an alkene of the formula (X). An alkene compound of the formula (X) is oxidized with an organic peracid such as meta-chloroperbenzoic acid in a suitable solvent such as methylene chloride to generate an epoxide of the formula (XI). An epoxide of the formula (XI) is reacted with an amine of the formula, R'NH-R$_7$, which amine can be used in excess and thus also serve as the reaction medium, optionally in the presence of water, at elevated temperature for a sufficient time to form an amino alcohol of the formula (XII). In some instances the opening of the epoxide to produce a compound of the formula (XII) proceeds such that one of the possible isomeric trans products of the formula (XII) is the predominate or exclusive product of the reaction. Reaction of an amino alcohol of the formula (XII) with methanesulfonyl chloride in the presence of a suitable acid scavenger such as triethylamine in a suitable organic solvent such as methylene chloride, preferably with external cooling, followed by reaction of the resulting compound with an amine of the formula, HNR'$_1$R'$_2$, which may be taken in excess and thus serve as the reaction medium, optionally in the presence of water, at elevated temperature for a sufficient time provides a mixture of two diamines of the formula (XIII), each having interchanged values of p and n relative to the other. (It is recognized that when p is equal to n, only one compound of the formula (XIII) is obtained.) Alternatively, when one of R' and R$_7$ is hydrogen, reaction of an amino alcohol of the formula (XII) with methanesulfonyl chloride, as described above, and then reaction of the resulting compound with aqueous sodium hydroxide at elevated temperature, affords an aziridine of the formula (XIV) which aziridine is reacted with an amine of the formula, HNR'$_1$R'$_2$, as described above, to give a mixture of two diamines of the formula (XIII), each having interchanged values of p and n relative to the other.

Reaction of an epoxide of the formula (XI) with an amine of the formula, $HNR'_1R'_2$, as described above, gives an amino alcohol of the formula (XV). In some instances the opening of the epoxide to produce an amino alcohol compound of the formula (XV) proceeds such that one of the possible isomeric trans products of the formula (XV) is the predominate or exclusive product of the reaction.

An amino alcohol of the formula (XV) is reacted with methanesulfonyl chloride, as described above, followed by reaction of the resulting product with an amine of the formula, $R'NH_2$, which may be taken in excess and thus serve as the reaction medium, optionally in the presence of water, at elevated temperature for a time sufficient to form a mixture of two diamines of the formula (XIII), each having interchanged values of p and n relative to the other.

A diamine of the formula (XIII) is reacted with a suitable acyl source as described above to produce an amino amide of this invention of the formula (XVI). An amino amide of the formula (XVI) is reacted with an aqueous mineral acid such as hydrochloric acid to give a ketone of this invention of the formula (XVII). Reduction of a ketone of the formula (XVII) with K-Selectride (potassium tri-sec-butylborohydride) in a suitable organic solvent such as tetrahydrofuran, preferably at low temperature, ($-75°$ to $0°$ C.) provides one hydroxy compound or two hydroxy compounds of this invention of the formula (XVIII) wherein one particular epimer at the hydroxyl-bearing cycloalkyl ring carbon atom usually is the more abundant or exclusive alcohol product. Alternatively, reduction of a ketone of the formula (XVII) with sodium borohydride in a suitable solvent such as ethanol at about $0°$ to $25°$ C. gives one compound or two compounds of this invention of the formula (XVIII), wherein the more abundant or exclusive alcohol product usually is the epimer opposite in configuration to that obtained from the K-Selectride reduction described above. Reaction of an alcohol of the formula (XVIII) with an appropriate acid chloride, acid anhydride or mixed anhydride in a suitable medium such as pyridine optionally at elevated temperature, preferably about $60°$, yields an ester of this invention of the formula (XIX).

Reaction of an alcohol of the formula (XVIII) with a base such as sodium hydride in a suitable solvent such as dimethylformamide followed by addition of a lower alkyl halide of the formula, $R_5Z$ (wherein Z is Cl, Br, or I), affords an ether of this invention of the formula (XX).

The process steps illustrated in Chart B are used to prepare compounds of this invention of the formulas (XXI), (XXII), (XXIII), and (XXIV). A ketone of the formula (XVII) (from Chart A) is reacted with an appropriate glycol of the formula, $HSCH_2—CH_2SH$, in the presence of boron trifluoride etherate ($BF_3OEt_2$) to give a dithioketal of this invention of the formula (XXI). A ketone of the formula (XVII) is reacted with a glycol of the formula, $HOCH_2—CH_2SH$, in the presence of $ZnCl_2$ and sodium sulfate or with said glycol in the presence of $BF_3.Et_2O$ to yield a compound of this invention of the formula (XXII). Alternatively compounds of the formulas (XXI) and (XXII) can be prepared by reaction of a ketone (XVII) with 1,2-ethanedithiol or 2-mercaptoethanol, respectively, in a suitable solvent such as benzene or toluene in the presence of an acid catalyst such as p-toluenesulfonic acid with azeotropic removal of the water formed. Reaction of a ketone of the formula (XVII) with hydroxylamine in the presence of sodium hydroxide produces an oxime of the formula (XXIII), which oxime is reacted with sodium hydride in a suitable solvent such as dimethylformamide followed by addition of acetyl chloride to the mixture to afford an acetoxime compound of this invention of the formula (XXIV).

There are no structures in this application bearing Roman numerals XXV to XXX.

A compound of formula (I), wherein at least one of X and Y is hydroxyl, is prepared as follows. A suitable ketone of the formula (XVII), wherein X and/or Y is methoxy, is reacted with boron tribromide in methylene chloride to produce a ketone of the formula (XVII) wherein the corresponding X and/or Y is hydroxyl, which hydroxyl compound can be further reacted as in Chart A, or which compound is converted to a ketal of the formula (XVI) by reaction with a glycol of the formula $HECH_2—CH_2EH$, using standard conditions well known in the art.

Cis compounds of this invention of the formula (I) are prepared as illustrated in part in Charts C and D. $R_8$ is $C_1$ to $C_3$-alkyl. Reaction of a ketone of the formula (VIII) with a suitable base such as sodium hydride in a suitable inert organic solvent such as DMF, followed by addition to the mixture of a lower alkyl chloroformate affords a keto ester of the formula (XXXI), which is reacted with an amine of the formula, $HNR'_1R'_2$, with azeotropic removal of water to produce an enamine of the formula (XXXII). Alternatively, a ketone of the formula (VIII) is converted to an enamine of the formula (XXXIII), which enamine is reacted with a lower alkyl chloroformate to give an enamine of the formula (XXXII). Hydrogenation of an enamine of the formula (XXXII) with hydrogen and a suitable catalyst such as platinum (from platinum oxide) in a suitable organic solvent such as ethyl acetate or a lower alkanol yields a cis amino ester of the formula (XXXIV). Reaction of an amino ester of the formula (XXXIV) with a suitable base such as an alkali metal hydroxide, for example, sodium or potassium hydroxide, followed by a Curtius reaction affords a diamine of the formula (XXXV). The Curtius reaction is conducted as described by P. W. Erhardt, J. Org. Chem., 44, 883 (1979) or as described by T. Shioiri, et al., J. Amer. Chem. Soc. 94, 6203 (1972) or the like. If R of a formula (I) compound being prepared is $C_1$ to $C_3$-alkyl, then a diamine compound of the formula (XXXV) is alkylated with a lower alkyl halide of the formula R-Z (wherein Z is Cl, Br or I) or acylated with an appropriate acid chloride, acid anhydride or mixed anhydride in a suitable medium such as pyridine optionally at elevated temperature, followed by diborane reduction according to H. C. Brown and P. Heim, J. Amer. Chem. Soc., 86, 3566 (1964), to generate a diamine of the formula (XXXVI). Reaction of a diamine of the formula (XXXVI) with a suitable acyl source as described above yields a compound of this invention of the formula (XXXVII). When one or both of $R_1$ and $R_2$ of a cis formula I compound being prepared using Chart C are to be allyl, suitable N protecting groups are used, and the allyl group or groups must be introduced after the enamine hydrogenation step. To prepare additional cis Formula I compounds of this invention, a compound of the formula (XXXVII) is analogously reacted: (1) as described in Chart A for the conversion of a compound of the formula (XVI) to compounds of the formulas (XVII), (XVIII), (XIX) and (XX); (2) as described in Chart B for the conversion of a ketone of the formula (XVII) to compounds of the formulas (XXI), (XXII), (XXIII) and (XXIV); and (3) as described elsewhere in this specification for a compound of the formula (XVII).
CHART C
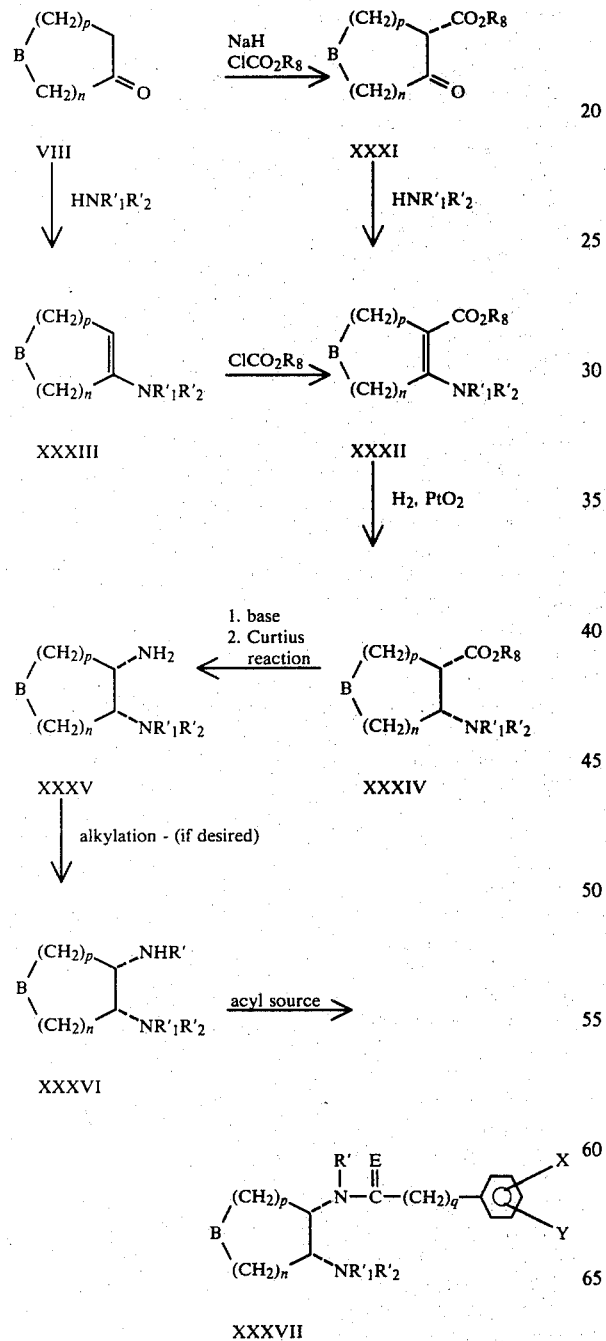
CHART D
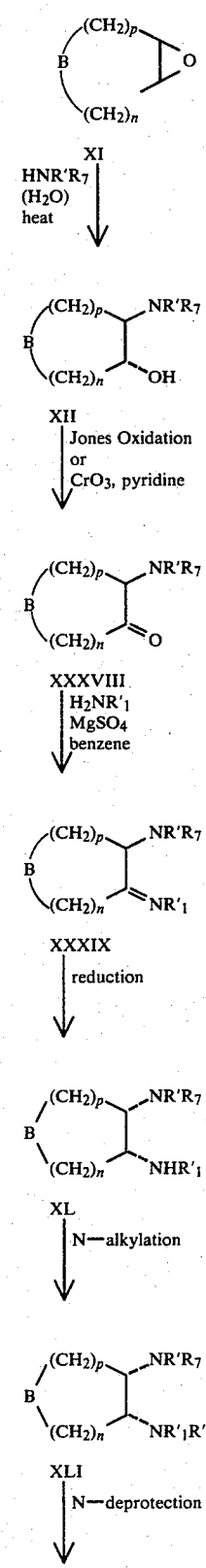

-continued
CHART D

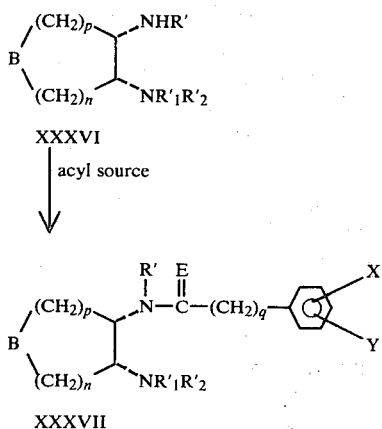

XXXVI acyl source

XXXVII

In addition, some of these cis compounds of the formula (I) are also prepared using an alternate process to produce a diamine of the formula (XXXVI) as illustrated in Chart D. As described for Chart A, an epoxide of the formula (XI) is prepared and converted to an amino alcohol of the formula (XII), which is oxidized using standard methods, for example, chromium trioxide ($CrO_3$)-sulfuric acid in acetone solvent at 0° (known as the Jones oxidation) or chromium trioxidepyridine, to afford a ketone of the formula (XXXVIII). A ketone of the formula (XXXVIII) is reacted with an amine of the formula, $H_2NR'_1$, in the presence of magnesium sulfate ($MgSO_4$) in a suitable organic solvent such as benzene to produce an imine of the formula (XXXIX). An imine of the formula (XXXIX) is reduced with a suitable reducing agent such as lithium aluminum hydride ($LiAlH_4$) or sodium cyanoborohydride ($NaBH_3CN$) to give a cis diamine of the formula (XL) admixed with the corresponding trans diamine. The reduction of imines with these reagents is described by D. A. Evans, et al., J. Amer. Chem. Soc., 100, 8170 (1978). The cis diamine of structure (XL) is separated from the trans isomer at this stage of the synthesis or a separation is performed at a later stage, for example, after the formation of a cis benzeneacetamide or benzamide compound of the formula (XXXVII) admixed with the corresponding trans isomer of the formula (XVI).

When $R_2$ of a formula (I) compound being prepared is other than hydrogen, or when $R_1$ and $R_2$ of a formula (I) compound being prepared, taken together with the nitrogen to which they are bonded complete an azetidinyl, pyrrolidinyl or piperidinyl ring, such nitrogen substitution is introduced at this stage of the synthesis using an alkylation of a diamine of the formula (XL), amine alkylations being well known in the art, to produce an alkylated diamine compound of the formula (XLI). An alkylated diamine of the formula (XLI) is deprotected to give a diamine of the formula (XXXVI) which is treated with a suitable acyl source as described above to afford a compound of this invention of the formula (XXXVII).

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combinations with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01mg per kg to about 5 mg per kg of body weight of the recipient. Preferred dosages for most applications are 0.05 to 2.0 mg per kg of body weight.

The useful pharmaceutical dosage unit forms of these compounds in pharmaceutical formulations are preferably adapted for systemic administration to obtain analgesic effects comprising an effective, non-toxic amount of a compound according to Formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmcological test procedures which measure analgesia and the physical dependence liability of the test compounds in standard laboratory test animals.

Representative examples of these Formula I compounds have $ED_{50}$ values of less than about 75 mg/kg s.c. (subcutaneous administration) in standard laboratory animal analgesic tests such as the tail flick, pinch, and hydrochloric acid writhing tests, and the more potent of them have $ED_{50}$ values of less than 10 mg/kg (s.c.) in these tests, while at the same time giving quite high values (greater than 250 mg/kg s.c.) in the naloxone jumping test thus possessing low apparent physical dependence liability as compared to commercial analgesics used as standards. The procedures used to determine these properties of these new compounds were essentially those of Way et al., (Way, E. L. et al., "Simultaneous Quantitative Assessment of Morphine Tolerance and Physical Dependence," J. Pharmacol. Exp. Ther., 167, pp. 1–8 (1969)) and Saalens et al., (Saalens, J. K. et al., "The Mouse Jumping Test—A Simple Screening Method to Estimate the Physical Dependence Capacity of Analgesics", Arch. Int. Pharmacodyn., 190, pp. 213–218 (1971)). Statistical effective doses ($ED_{50}$ values) and 95% confidence limits were calculated by the method of Spearman and Karber (Finney, D. J., "Statistical Methods in Biological Assay," Hafner Publ., (1952)).

For example, representative preferred compounds of Formula I give low analgesic $ED_{50}$ values (less than about 10 mg of test compound/kg of animal body weight, subcutaneous administration route) in standard laboratory animal tests while at the same time possessing quite high $ED_{50}$ values (greater than 250 mg/kg s.c.) in the naxolone jumping test, evidencing substantial freedom from apparent physical dependence liability. In contrast, known analgesic drugs such as morphine and methadone exhibit analgesic $ED_{50}$ values of less than 2 mg/kg s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg/kg s.c. Other representative compounds of this invention have analgesic potencies somewhat less than the preferred compounds (an analgesic activity $ED_{50}$ values up to about 75 mg/kg s.c., in these standard tests), and some such compounds still are characterized by having only low to moderate apparent physical dependence liability.

The invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, IR (or ir) means infrared spectrum points of reference, m/e means the mass of a mass spectral fragment divided by its charge, M+ means the mass corresponding to the parent molecular ion, $CH_2Cl_2$ means methylene chloride solvent, $K_2CO_3$ or $Na_2SO_4$ means the organic layer was dried over anhydrous forms of these salts, mp means melting point, NMR (or nmr) means nuclear magnetic resonance spectrum and NMR ($CDCl_3$) means a nuclear magnetic resonance spectrum made using deuteriochloroform as a solvent and values in parts per million are reported as downfield shifts from a tetra-methylsilane internal reference; DBN means 1,5-diazabicyclo[4.3.0]non-5-ene; h means hour(s), $N_2$ means nitrogen, tlc means thin layer chromatography procedures, $Na_2SO_3$ means sodium sulfite, $NaHCO_3$ means sodium bicarbonate, DMSO is dimethylsulfoxide, Skellysolve B (or Skelly B) is a tradename for a solvent of essentially n-hexane, bp 60°–68° C. (Merck Index, Ninth Edition (1976) page 1106), $Et_2O$ means diethyl ether, MeOH means methanol, THF means tetrahydrofuran, $H_2O$ means water, $CHCl_3$ means chloroform, brine is saturated aqueous sodium chloride solution, DMF means N,N-dimethylformamide, $Et_3N$ is triethylamine, HRMS means high resolution mass spectrum, EtOAc means ethyl acetate; HCl mens hydrogen chloride.

EXAMPLE 1

Preparation of trans-3,4-dichloro-N-methyl-N-[8-(1-pyrrolidinyl)-1,4-dioxaspiro[4.5]dec-7-yl]benzeneacetamide and trans-3,4-dichloro-N-methyl-N-[7-(1-pyrrolidinyl)-1,4-dioxaspiro[4.5]dec-8-yl]benzeneacetamide A. 8-Hydroxy-1,4-dioxaspiro[4,5]decane A mixture of 4-hydroxycyclohexanone (228 g, 2.0 mol) ethylene glycol (124 g, 2.0 mol) and p-toluenesulfonic acid monohydrate (0.89 g) in 2.0 l of benzene was stirred at reflux in a 3-l, three-necked, round-bottomed flask equipped with a Dean-Stark trap. The mixture was refluxed until the required amount of water had been removed. Solvent was removed by distillation and the residue was fractionally distilled at 85°–88.5° C. (0.08 mm Hg.) to give 247.8 g of the sub-titled intermediate. (78%), Lit bp 90°–95° C. (0.2 mm Hg.). (M. I. Batuev, et al., Ixvest. Akad. Nauk S.S.S.R., Otdel, Khim Nauk, 1960, 538–549.) IR, OH (3420), C-O (1105, 1035, 920); mass spectrum, m/e 158 (M+).

Anal. Calcd. for $C_8H_{14}O_3$: C, 60.74; H, 8.92, Found: C, 60.28; H, 9.23.

B. 8-Tosyloxy-1,4-dioxaspiro[4.5]decane

A mixture of 8-hydroxy-1,4-dioxaspiro[4.5]decane (237 g, 1.5 mol) and 700 ml of pyridine was stirred at 0° C. while p-toluenesulfonyl chloride was added portionwise. After the addition was completed the mixture was stirred for two days at 7° C. The mixture was poured into a 4-kg mixture of equal parts of ice and water with vigorous stirring. After about fifteen minutes a solid separated; this was filtered and washed with water.

Dissolved the solid in $CH_2Cl_2$ and separated $CH_2Cl_2$ solution from residual water. The organic layer was dried ($K_2CO_3$-$Na_2SO_4$), filtered and concentrated in vacuo at 36° C. The solution remaining was diluted with Skellysolve B and cooled to $-75°$ C. with stirring. The white solid was filtered and dried in vacuo to give 435 g (92.9%), mp 65°–67.5° C. of the sub-titled intermediate. IR C=C (1600), $-SO_2O-$ (1350, 1180), C—O/S—O—C (1105, 945, 925), $-SO_3-$ (675); nmr ($CDCl_3$) was in accordance with the structure assignment; mass spectrum m/e 312 (M+).

Anal. Calcd. for $C_{15}H_{20}SO_5$: C, 57.67; H, 6.45; S, 10.27, Found: C, 57.06; H, 6.30; S, 10.17.

C. 1,4-Dioxaspiro[4.5]dec-7-ene

Method A. 8-Tosyloxy-1,4-dioxaspiro[4.5]decane (62.4 g, 0.2 mol) was added portion-wise to diazabicyclo[4.3.0]non-5-ene (DBN) (27.3 g, 0.22 mol) at ambient temperature. When the addition was completed the suspension was heated to 89° C. and the heat source was removed. The reaction temperature continued to rise and reached 116° C. before it began to fall. The mixture was stirred at 100° C. for one hour and forty-five minutes before cooling the mixture, diluting with water, and extracting with hexane. The hexane extracts were washed with 100 ml of saturated salt solution, dried ($Na_2SO_4$), and concentrated to a light yellow liquid. The crude olefin weighed 21 g (75%), Distillation at reduced pressure gave 15.15 g (54%) of the sub-titled olefin at 111.5–113° C./25 mm. IR, =CH (3020), C=C (1655), C-O (1110, 1060, 1030); nmr ($CDCl_3$) was in accordance with the structure assignment; mass spectrum m/e 140 (M+).

Anal. Calcd. for $C_8H_{12}O_2$: C, 68.54; H, 8.63, Found: C, 68.62; H, 8.91.

Method B. A mixture of 8-toxyloxy-1,4-dioxaspiro[4.5]decane (20.8 g, 0.067 mol), sodium bicarbonate (6.5 g, 0.077 mol), and 100 ml of DMSO was stirred at 95° C. for 20 h under $Na_2$ atmosphere. When the mixture had cooled to room temperature it was diluted with 100 ml of water and extracted with $3 \times 200$ ml of Skellysolve B. The extracts were washed with 100 ml of water, dried ($Na_2SO_4$), and concentrated in vacuo to a pale yellow liquid, 6.9 g (74%). The material (subtitled olefin) was nearly pure by tlc and nmr analyses and identical to olefin prepared as by Method A.

D.

Spiro[7-oxabicyclo[′.1.0]heptane-3,2′-[1,4]-dioxolane]m-Chloroperoxybenzoic acid. (85%, 32.9 g, 0.163 mol) in 418 ml of $CH_2Cl_2$ was added dropwise to a stirred and cooled ($-5°$ to 0° C.) mixture of 1,4-dioxaspiro[4.5]dec-7-ene (21.2 g, 0.151 mol) in 150 ml of $CH_2Cl_2$ and stirred for three days at ambient temperature. A 10% solution of $Na_2SO_3$ (111 ml) was added dropwise to the ice-cooled mixture until a negative test with starch-iodide paper indicated no peracid was present. The insoluble benzoic acid was removed by filtration and the mixture was extracted with 250 ml of 6% $NaHCO_3$, washed with brine, and dried ($Na_2SO_4$). Removal of solvent in vacuo gave 24.7 g of nearly pure material (the sub-titled epoxy compound). Distillation of the liquid at 54°–56° C./0.1 mm Hg. gave 17.6 g (74.8%) of this material as a clear liquid. Nmr ($CDCl_3$) is in accordance with the structure assignment and the mass spectrum indicates a fragment at m/e 155 (M+ −1).

Anal. Calcd. for $C_8H_{12}O_3$: C, 61.52, H, 7.75, Found: C, 61.48; H, 8.08.

E. trans-8-Hydroxy-7-(methylamino)-1,4-dioxaspiro[4.5]-decane

A mixture of spiro 7-oxabicyclo[4.1.0]heptane-3,2′-[1,4]-dioxolane] (101 g, 0.65 mol) and 40% aqueous methylamine (151 g, 1.94 mol) was stirred at ambient temperature for forty-eight hours, then heated on a steam bath for two hours. The mixture was cooled with an ice-water bath while being saturated by addition of solid NaOH. A dark upper layer separated from the mixture and this was removed. The aqueous layer was extracted with $CHCl_3$ and the $CHCl_3$ extracts were added to the dark layer mentioned above. The mixture was dried ($Na_2SO_4$) and concentrated in vacuo to a dark liquid. Distillation at 115°–117° C./0.35 mm Hg. gave 89 g (73.5%). Distillation of the residue on a Kugelrohr apparatus at 105° C./0.03 mm Hg. gave an additional 12.6 g (10.4%). Total yield of the subtitled amine product is 83.9%. Mass spectrum m/e 187 (M+), nmr, and ir are consistent with the structure assignment.

Anal. Calcd. for $C_{19}H_{17}NO_3$: C, 57.73; N, 9.15; N, 7.48, Found: C, 57.51; N, 9.08; N, 7.51.

F. 7-Methylspiro[7-azabicyclo[4.1.0]heptane-3,2′-[1,4]-dioxolane]

A mixture of trans-8-hydroxy-7-(methylamino)-1,4-dioxaspiro-[4,5]decane (141.9 g, 0.76 mol) in 2.5 l of $CH_2Cl_2$ was stirred under $N_2$ atmosphere at $-8°$ to $-4°$ C. while chlorosulfonic acid (49.4 ml, 88.4 g, 0.76 mol) was added dropwise. The cooling bath was removed after, the addition was completed and the mixture was stirred at ambient temperature for two days. The flask was modified for distillation and $CH_2Cl_2$ was removed on a steam bath. Aqueous sodium hydroxide (1.1 N, 1.5 l) was added and the mixture was stirred and heated on a steam bath for twenty-seven hours. The cooled solution was extracted extensively with $CHCl_3$ and the extracts were washed successively with liter portions of water and saturated NaCl solution. Removed the solvent on a rotary evaporator and distilled at reduced pressure to give 61 g (49.6%) of the liquid subtitled product at 46.5°–52° C./0.05–0.065 mm Hg. mass spectrum m/e 169 (M+), nmr, and ir are consistent with the structure assignment.

Anal. Calcd. for $C_9H_{15}NO_2$: C, 63.86; H, 8.94; N, 8.28, Found: C, 63.21; H, 9.22; N, 8.35.

G.
trans-7-(N-Methylamino)-8-(1-pyrrolidinyl)-1,4-dioxaspiro[4.5]decane and trans-8-(N-Methylamino)-7-(1-pyrrolidinyl)-1,4-dioxaspiro[4.5]decane Method A. A mixture of 7-methylspiro[7-azabicyclo[4.1.0]-heptane-3,2'-[1,4]dioxolane] (28 g, 0.166 mol), pyrrolidine (56 ml, 47.6 g, 0.67 mol), ammonium chloride (0.56 g), and water (35 ml) was refluxed for a total of fifty-nine hours under $N_2$ atmosphere. The mixture was cooled in an ice-water bath and saturated with NaOH pellets. Extraction of the mixture with $CHCl_3$ and removal of $CHCl_3$ in vacuo gave 45.4 g of crude product contaminated with residual pyrrolidine. Distillation at reduced pressure gave 35.3 g (88%) of the subtitled isomer mixture material at 102°–104° C./0.02 mm Hg. Mass spectrum indicates an ion fragment at m/e 240 (M+). Nmr and ir spectra are consistent with the structure assignment.

Anal. Calcd. for $C_{13}H_{24}N_2O_2$: C, 64.96; H, 10.06; N, 11.66, Found: C, 63.64; H, 9.96; N, 11.32.

Method B. Spiro[7-oxabicyclo[4.1.0]heptane-3,2'-[1,4]dioxolane] was reacted with methyl(phenylmethyl)amine in the presence of water at 90° C. to give a 92% yield of trans-7-[methyl(phenylmethyl)amino[-1,4-dioxaspiro[4.5]decan-8-ol, bp 158°–161° C. (0.005 mm Hg). This amino alcohol was reacted with methanesulfonylchloride in the presence of triethylamine in methylene chloride solution at 0° C., and the resulting sulfonate ester was reacted with pyrrolidine in the presence of water at 90° C. to give a mixture of diamines, which were debenzylated by hydrogenation using a palladium on carbon catalyst to give a mixture (approximately 1:1 by nmr) of the subtitled diamines. The yield is 74% from the starting amino alcohol.

H.
trans-3,4-Dichloro-N-methyl-N-[8-(1-pyrrolidinyl)-1,4-di-oxaspiro[4.5]dec-7-yl]benzeneacetamide (Isomer 1) and trans-3,4-dichloro-N-methyl-N-[7-(1-pyrrolidinyl)-1,4-dioxaspiro[4.5]dec-8-yl]-benzeneacetamide (Isomer 2)

Method A. A mixture of trans-7-(N-methylamino)-8-(1-pyrrolidinyl)-1,4-dioxaspiro[4.5]decane and trans-8-(N-methylamino)-7-(1-pyrrolidinyl)-1,4-dioxaspiro[4.5]-decane (64 g, 0.28 mol), triethyl-amine (39 ml, 28.3 g, 0.28 mol) and 280 ml of ether was added dropwise to a solution of 3,4-dichlorophenylacetyl chloride (65.7 g, 0.29 mol) in 280 ml of ether. The mixture was stirred for sixty-four hours and quenched by dropwise addition of 60 ml water. The mixture was neutralized by addition of 60 ml of 10% NaOH solution and extracted with $CHCl_3$. The combined organic extracts were washed with water, dried ($Na_2SO_4$), and concentrated in vacuo to give an oil (147 g). The oil was dissolved in $CHCl_3$, diluted with $Et_2O$, and refrigerated to give 37 g of nearly pure isomer 1 compound, the more polar amide. Recrystallization of this material from $CHCl_3$—$Et_2O$ gave 17.4 g, mp 93°–95° C. of isomer 1 compound and 19.1 g of an oil. The oil was combined with the original filtrates and the mixture chromatographed over 5 kg of $SiO_2$ with $NH_4OH:MeOH:CH_2Cl_2$ (0.25:1.1:98.65%) to give 12.7 g (10.6%), mp 91°–94° C. of isomer 2 compound which was recrystallized from $Et_2O$—Skellysolve B. An additional 9.7 g of isomer 1 was obtained giving a total of 27.1 g (22.5%). Impure fractions were set aside for later purification. Isomer 2 had mass spectrum m/e 427/429 (M+1, chlorine isotopic peaks). Nmr and ir spectra were consistent with the structure assignment.

Anal. Calcd. for $C_{21}H_{28}Cl_2N_2O_3$: C, 59.02; H, 6.60; Cl, 16.59; N, 6.56, Found: C, 59.03; H, 6.48; Cl, 17.07; N, 6.59.

Isomer 1 had mass spectrum m/e 426/428 (M+, chlorine isotopic peaks). Nmr and ir spectra were consistent with the structure assignment.

Anal. Calcd. for $C_{21}H_{28}Cl_2N_2O_3$: C, 59.02; H, 6.60; Cl, 16.59; N, 6.56, Found: C, 59.33; H, 6.57; Cl, 17.12; N, 6.69.

Method B. As an alternative to Method A, above, a mixture of the diamines (24.7 g) prepared as described in Part G above was reacted with 3,4-dichlorophenylacetyl imidazolide (from 3,4-dichlorophenylacetic acid and N,N'-carbonyldiimidazole) in tetrahydrofuran at 20°–25° C. to give a mixture of the titled amino amides. Fractional crystallization of the crude product from diethyl etherhexane mixture afforded 10.2 g of Isomer I, 9.0 g of Isomer 2, and 11.0 g of a mixture of Isomers 1 and 2. The amino amides produced by this Method were identical to those produced in Method A above.

EXAMPLE 2

Preparation of trans-3,4-dichloro-N-methyl-N-[4-oxo-2-(1-pyrrolidinyl)cyclohexyl]benzeneacetamide A mixture of trans-3,4-dichloro-N-methyl-N-[7-(1-pyrrolidinyl)-1,4-dioxaspiro[4.5]dec-8-yl]benzeneacetamide (12.3 g, 0.029 mol) from Example 1, 3 N HCl solution (288 ml), and 432 ml of acetone was stirred at 60° C. under $N_2$ atmosphere for one hour. Acetone was removed on a rotary evaporator and the mixture was extracted with chloroform. The chloro-form extracts were dried ($Na_2SO_4$), concentrated in vacuo and diluted with ether. Refrigeration overnight gave white crystals which were dried at 60° C. in vacuo for two days to give 10.5 g (87%) of the titled compound, mp 148.0°–148.9° C. The mass spectrum indicated ion fragments at m/e 382/384 (M+, chlorine isotopic peaks). The ir and nmr spectra were consistent with the structure assignment.

Anal. Calcd. for $C_{19}H_{24}Cl_2N_2O_2$ HCl: C, 54.36; H, 5.76; Cl, 25.34; N, 6.67, Found: C, 53.85; H, 6.19; Cl, 25.39; N, 7.02.

EXAMPLE 3

Preparation of (1α,2β,4α)-N-[4-(acetyloxy)-2-(1-pyrrolidinyl)cyclohexyl]-3,4-dichloro-N-methylbenzeneacetamide hydrochloride

A.
(1α,2β,4α)-3,4-Dichloro-N-methyl-N-[4-hydroxy-2-(1-pyrrolidinyl)cyclohexyl]benzeneacetamide hydrochloride trans 3,4-dichloro-N-methyl-N-[4-oxo-2-(1-pyrrolidinyl)-cyclohexyl]benzene-acetamide hydrochloride (8.4 g, 0.0198 mol) from Example 2 was suspended in 160 ml of dry tetrahydrofuran in a three-necked, R.B. flask inerted with $N_2$ and the suspension was cooled to −78° C. A solution of 160 ml of 0.25 M. potassium tri-sec-butylborohydride in tetrahydrofuran was added dropwise to the suspension at −78° C. When the addition was completed the cooling bath was removed and the mixture was stirred for 2.5 hours. O$_2$-free MeOH (20 ml) was added followed by addition of 20 ml of O$_2$-free H$_2$O. The mixture was acidified by addition of 180 ml of 2.5 N HCl solution. Extracted the mixture with diethyl ether and backwashed the ether extracts with H$_2$O. The aqueous phases were combined and extracted with CHCl$_3$ (8×250 ml). The CHCl$_3$ extracts were washed with 250 ml of brine and dried (Na$_2$SO$_4$). Evaporation of solvent in vacuo gave the subtitled salt as an off-white solid (8.1 g). The solid was crystallized from CHCl$_3$-MeOH, CHCl$_3$-EtOH-Et$_2$O, and EtOH-Et$_2$O to give three crops of solid weighing 2.5, 3.7, and 0.4 g, respectively. Combined yield of the three crops was 78.5% of the subtitled compound, m.p. 238.9°–244.9° C. Mass spectrum m/e 384/386 (M+, chlorine isotopic peaks). IR, OH (3320 cm$^{-1}$), NH+ (2640), C=O (amide, 1645) and nmr spectra were consistent with the structure assignment for the titled hydroxy compound.

Anald. Calcd. for C$_{19}$H$_{26}$Cl$_2$N$_2$O$_2$1 1HCl: C, 53.63; H, 6.16; Cl, 25.83; N, 6.59, Found: C, 53.61; H, 6.44; Cl, 25.79; N, 6.88.

B.

1α,2β,4α)-N-[4-acetyloxy-2-(-pyrrolidinyl)cyclohexyl]-3,4-dichloro-N-methyl-benzeneacetamide hydrochloride A mixture of (1α,2β,4α)-3,4-dichloro-N-methyl-N-[4-hydroxy-2-(1-pyrrolidinyl)cyclohexyl]benzeneacetamide hydrochloride (1.5 g, 0.036 mol), pyridine (90 ml), acetic anhydride (90 ml) and 45 ml of chloroform was stirred at 60° C. for 1.5 hours under N$_2$. Dilution of the mixture to 800 ml with diethyl ether and refrigeration gave 1.2 g (79%) after drying overnight at 77° C. in vacuo, mp 259.5°–264.1° C. Mass spectrum m/e 426/428 (M+, chlorine isotopic peaks). IR, NH+ (2560, 2520, 2480 cm$^{-1}$) and nmr were consistent with the structure assignment of the titled acetoxy compound.

Anal. Calcd. for C$_{21}$H$_{28}$Cl$_2$N$_2$O$_3$ HCl: C, 54.38; H, 6.30; Cl, 22.93; N, 6.04, Found: C, 54.19; H, 6.20; Cl, 22.83; N, 6.10.

EXAMPLE 4

(1α,2β,5β)-N-[5-(acetyloxy)-2-(1-pyrrolidinyl]cyclohexyl]-3,4-dichloro-N-methylbenzeneacetamide monohydro-chloride

A.

trans-3,4-Dichloro-N-methyl-N-[5-oxo-2-(1-pyrrolidinyl)cyclohexyl]benzeneacetamide hydrochloride A mixture of trans-3,4-dichloro-N-methyl-N-[8-(1-pyrrolidinyl)-1,4-dioxaspiro[4.5]dec-7-yl]benzeneacetamide (4.5 g, 0.01 mmole) prepared by procedures described above, and 100 ml of 3 N HCl solution was stirred under N$_2$ atmosphere while 150 ml of acetone was added. The mixture was stirred at 58° C. for one hour and cooled to room temperature. Removed the acetone in vacuo and neutralized the mixture by addition of solid NaHCO$_3$ with intermittant cooling of the mixture in a dry ice-acetone bath. Extracted the aqueous layer with CHCl$_3$; the CHCl$_3$ extracts were dried (Na$_2$SO$_4$) and concentrated in vacuo to a pale yellow oil (5 g). Dissolved the oil in CHCl$_3$ and treated the solution with ethereal HCl. Separated the solvent from a pale yellow gum and dissolved the gum in CHCl$_3$. Diluted the CHCl$_3$ solution with ether and refrigerated overnight. Filtered the white solid which deposited and dried in vacuo at 40° C. to give a total of 4.95 g of the titled cyclohexanone. Mass spectrum m/e 382/384 (M+, chlorine isotopic peaks). IR NH (2600, 2480), C=O (ketone) 1725, C=O (amide) 1645 cm$^{-1}$ and nmr spectra were consistent with the structure assignment.

Anal. Calcd. for C$_{19}$H$_{24}$Cl$_2$N$_2$O$_2$ 2.7 HCl: C, 47.28; H, 5.01; Cl, 34.53; N, 5.81. Found: C, 47.35; H, 5.41; Cl, 34.31, N, 5.77.

B.

(1α,2β,5β)-3,4-dichloro-N-[5-hydroxy-2-(1-pyrrolidinyl)-cyclohexyl]-N-methylbenzeneacetamide monohydrochloride Trans-3,4-dichloro-N-methyl-N-[5-oxo-2-(1-pyrrolidinyl)cyclohexyl]benzeneacetamide hydrochloride (8 g, 0.019 mole) was suspended in 160 ml of dry tetrahydrofuran in a 500-ml three-neck, round-bottom flask which was inerted with N$^2$. To this suspension cooled to −78° C. was added dropwise a solution of 76.5 ml of 0.5 M potassium tri-sec-butylborohydride in THF diluted to 153 ml with dry THF. When the addition was completed, the cooling bath was removed and the mixture was stirred for 1.5 hours. TLC analysis indicated that all of the ketone had reacted. The mixture was cooled in an ice water bath and successively diluted dropwise with 20 ml of oxygen-free methanol and 20 ml of oxygen-free water. The mixture was acidified with 180 ml of 2.5 N aqueous hydrochloric acid and extracted with 100 ml of diethyl ether. The ether extracts were back-extracted with 60 ml of water, and the combined aqueous extracts were extracted four times with CHCl$_3$ (250 ml portions). The CHCl$_3$ extracts were dried (Na$_2$SO$_4$), concentrated in varuo, and refrigerated to give (after drying in vacuo at 67° C.) 5.1 g (64%) of the subtitled white solid alcohol, mp 252.8°–253.4° C. Mass spectrum m/e 384/386 (M+, chlorine isotopic peaks). IR (OH(3320), NH (2620), C=O (amide 1635 cm-1) and nmr spectra were consistent with the structure assignment. The sample retains some chloroform and water.

Anal. Calcd. for C$^{19}$H$^{26}$Cl$^2$N$^2$O$^2$ HCl 1.10% CHCl$^3$ 0.12% H$^2$O: C, 53.44; H, 6.37; Cl, 25.47; N, 6.56. Found: C, 53.46; H, 6.56; Cl, 25.78; N, 6.49.

C.

(1α,2β,5β)-N-[5-(Acetyloxy)-2-(1-pyrrolidinyl)cyclohexyl]-3,4-dichloro-N-methylbenzeneacetamide monohydrochloride A mixture of (1α,2β,5β)-3,4-dichloro-N-[5-(hydroxy-2-(1-pyrrolidinyl)cyclohexyl]-N-methylbenzeneacetamide monohydrochloride (3 g, 0.007 mol) from Part B, above, pyridine (90 ml), acetic anhydride (90 ml), and 90 ml of chloroform was stirred at 60° C. for one hour under N$_2$. Removed the oil bath and stirred the mixture overnight. Removed some solvents at reduced pressure and diluted the remaining solution to 2 l with diethyl ether and filtered off the red solid HCl salt. Dissolved the solid in chloroform, treated the solution with charcoal and diluted with ether. Refrigeration and filtration gave a slightly yellow product, 2.5 g (84%). Recrystallization from CHCl$_3$-Et$_2$O gave 1.9 g (58%) and 0.2 g (6%) of the titled white solid salt, mp 168.0°–170.0° C. Mass spectrum m/e 426/428 (M+, chlorine isotopic peaks); HRMS, exact mass measurement: calcd, found 426.1468, IR, NH(2540, 2680 cm$^{-1}$) C=O (ester, 1730 cm$^{-1}$) and nmr are consistent with the structure assignment. Microanalyses indicates the compound is solvated by H₂O and HOAc.

Anal. Calcd. for $C_{21}H_{28}Cl_2N_2O_3$ HCl: C, 54.38; H, 6.30; Cl, 22.93; N, 6.04 MW 426, 1477, Found: C, 53.19; H, 6.17; Cl, 22.84; N, 5.98.

EXAMPLE 5 trans-(±)-4-bromo-N-[7-(dimethylamino)-1,4-dioxaspiro[4.5]dec-8-yl]-N-methylbenzamide monohydrochloride and
trans(±)-4-bromo-N-[8-(dimethylamino)-1,4-dioxa spiro-[4.5]dec-7-yl]-N-methylbenzamide

A.
trans-7-(Dimethylamino)-1,4-dioxaspiro[4.5]decan-8-ol

A mixture of 25.0 g (0.16 mol) of spiro[7-oxabicyclo[4.1.0]-heptane-3,2'-[1,3]-dioxolane] from Example 1, Part D, and 87.0 ml (0.05 mol) of of 40% aqueous dimethylamine was heated in an oil bath at 90° for four hours. The reaction mixture was cooled to 0° and were treated with NaOH pellets until two phases separated. Methylene chloride ($CH_2Cl_2$) was added, the phases were separated, the aqueous phase was extracted twice with $CH_2Cl_2$, the combined organic phases were dried ($MgSO_4$) and the solvent removed in vacuo leaving 31.0 g of a yellow liquid. The crude yellow liquid product thus obtained was distilled at reduced pressure through a short path to give 28.0 g (88%) of the subtitled aminoalcohol: bp 83°-87° (0.2 mm); IR (nujol) 3460 (OH) cm⁻¹, 2780 (N—C—H), 1134, 1090, 1050, 1040, 925 (C-O); mass spec. m/e 201 (M+). nmr (CDCl₃); 54.7 (S, 1H, OH), 3.95 (S, 4H, O(CH₂CH₂O), 3.1-3.5 (m, 1H, CH-OH), δ2.3-2.7 (m, 1H, CH—N), 2.25 (S, 6H, N(CH₃)₂)₂, 1-2 (m, 6H, ring CH₂). The IR and nmr spectra were in agreement with the structure assignment.

Anal. Calcd. for $C_{10}H_{19}NO_3$: C, 59.67; H, 9.52; N, 6.96, Found: C, 59.87; H, 9.93; N, 6.92.

B. trans-N⁷,N⁷, N⁸-trimethyl-1,4-dioxaspiro[4.5]-decane-7,8-diamine and trans-N⁷, N⁸, N⁸-trimethyl-1,4-dioxospiro[4.5]-decane-7,8-diamine A solution of 24.0 g (0.12 ml) of the amino alcohol from Part A and 14.5 g (0.13 mol) of Et₃N in 200 ml of CH₂Cl₂ was cooled to 0° and a solution of 15.1 g (0.13 mol) of methanesulfonyl chloride in 50 ml of CH₂Cl₂ was added dropwise over ca. 0.5 hr period. After the addition was complete the reaction mixture was stirred at 0° for two hours and distributed between ice cold H₂O and CH₂Cl₂. The phases were separated, the aqueous phase was extracted with CH₂Cl₂, the combined organic phases were dried (MgSO₄) and the solvent removed in vacuo at ambient temperature leaving 33 g of light yellow solid.

Approximately 31 g of the crude light yellow solid mesylate was transferred to a stainless steel bomb and 250 ml of freshly condensed methylamine was added. The bomb was sealed and then heated on a steam bath for sixty hours, cooled to 0° and opened and the excess methylamine was evaporated with a stream of nitrogen (N₂). The residue was distributed between CH₂Cl₂ and 5% sodium hydroxide (NaOH). The phases were separated, and the aqueous phase was extracted twice with CH₂Cl₂, the combined organic phases were dried (MgSO₄) and the solvent removed in vacuo leaving 24.4 g of brown liquid. The crude product was distilled at reduced pressure through a short path to give 20.75 g (78%) of a mixture of the subtitled diamines (G.C. suggests a 35:65 mixture): bp 88°-89° C. (0.1 mm). This diamine mixture was of suitable purity to be used without further purification.

C.
trans-(±)-4-Bromo-N-[7-(dimethylamino)-1,4-dioxaspiro[4.5]dec-8-yl]-N-methylbenzamide monohydrochloride (Isomer A) and
trans-(±)-4-Bromo-N-[8-(dimethylamino)-1,4-dioxaspiro[4.5]dec-7-yl]-N-methylbenzamide (Isomer B)

To a solution of 5.0 g (23.4 mmol) of diamine mixture from Part B and 2.7 g (24.5 mmol) of triethylamine (Et₃N) in 100 ml of dry ethyl Et₂O was added dropwise over a period of ca. one hour a solution of 5.38 g (24.5 mmol) of 4-bromobenzoyl chloride in 50 ml of Et₂O. After the addition was complete, the reaction mixture was stirred at ambient temperature for two hours and then filtered. The filtrate was distributed between ethyl acetate (EtOAc) and water (H₂O), the phases were separated, the aqueous phase extracted with EtOAc, the combined organics were washed with brine, dried (MgSO₄) and the solvent removed in vacuo, leaving 9.0 g of crude product.

A 2.5 g aliquot of the crude product was chromatographed on silica gel (Merck Lobar column) to give 0.9 g of pure titled Isomer A, and 0.9 g of pure titled Isomer B and mixed end fractions.

Isomer A was treated with ethereal hydrogen chloride (HCl) and the resultant precipitate collected and recrystallized twice from MeOH-Et₂O to give the titled Isomer A as a white hygroscopic salt: mp 185°-187°; IR (nujol) 3460, 3380 (OH,NH), 2680, 2470 (NH), 1640, 1600 (C=O,C=C), 1595, 1565 (C=C); mass spec. m/e 142 ((CH₃)₂ N⁺=CHCH=C—OCH₂CH₂O). The spectral evidence was consistent with the structure assigned.

Anal Calcd. for $C_{18}H_{26}ClBrN_2O_3$ 0.25 H₂O: C, 49.32; H, 6.09; Cl, 8.08; Br, 18.23; N, 6.39, Found: C, 49.38; H, 6.37; Cl, 7.97; Br, 18.04; N, 6.40.

Isomer B crystallized as the free base to give after two recrystallizations from Et₂O-hexane, the titled Isomer B: mp 119°-120°; IR (nujol) 2780 (N—C—H) cm⁻¹, 1630 (C=O); 1590, 1565 (C=C); mass spec., m/e 396,398 (M+), 84 ((CH₃)₂N=CHCH=CH₂), NMR (CDCl₃), δ1.0-2.0 (m, 6H, CH₂-ring) 2.0, 2.3 (S, 6H, (CH₃)₂N), 2.74, 2.90 (CH₃NCO), δ3.5-4.1 (m, 5H, CH₂O, CH-N(CH₃)₂), δ4.8 (m, 1H, CH-NCH₃CO) 7.2-7.6 (m, 4H, ArH). The spectral evidence was consistent with the structure assigned.

Anal. Calcd. for $C_{18}H_{25}BrN_2O_3$: C, 54.41; H, 6.34; N, 7.05; Br, 20.11, Found: C, 54.80; H, 6.43; N, 7.06; Br, 19.87.

EXAMPLE 6 trans-3,4-Dichloro-N-[7-(dimethylamino)-1,4-dioxaspiro[4.5]dec-8-yl]-N-methylbenzeneacetamide, (Isomer A) maleate salt, and
trans-3,4-Dichloro-N-[8-(dimethylamino)-1,4-dioxaspiro[4.5]dec-7-yl]-N-methylbenzeneacetamide, (Isomer B) maleate salt To a solution of 4.6 g (21.3 mmol) of diamine mixture from Example 5, Part B, and 2.5 g (23.5 mmol) of Et₃N in 150 ml of dry Et₂O was added dropwise a solution of 5.25 g of 3,4-dichlorophenylacetyl chloride in 50 ml of dry Et₂O. After the addition was complete, the reaction mixture was stirred at ambient temperature for two hours and then filtered. The filtrate was distributed between EtOAc and H$_2$O, the phases were separated, the aqueous phase was extracted with EtOAc, the combined organics were washed with brine, dried (MgSO$_4$) and the solvent removed in vacuo leaving 7.5 g of crude product. Two chromatographies of a 4.5 g aliquot of this crude product on silica gel (Merck lobar column) eluting with NH$_3$:MeOH:EtOAc, 0.4:3.6:96 (v:v) led to isolation of 1.7 g of the pure titled Isomer A and 1.6 g of the pure titled Isomer B along with mixed fraction of 1.0 g.

Isomer A was treated with maleic acid to give after two recrystallizations from EtOAc the pure maleate of Isomer A, mp 118°-121°; IR (nujol) 3460 (OH,NH) cm$^{-1}$, 2720, 2450, (HN$^+$, acid OH), 1735, 1700, 1630, 1580, (C=O, CO$_2{}^-$, C=C), 1480 (C=C); mass spec. m/e 142 ((CH$_3$)$_2$N$^+$=CHCH=C-OCH$_2$CH$_2$O). The spectral evidence was consistent with the structure assigned.

Anal. Calcd. for C$_{23}$H$_{30}$Cl$_2$N$_2$O$_7$: C, 53.39; H, 5.84; N, 5.41; Cl, 13.70, Found: C, 52.99; H, 6.22; N, 5.31; Cl, 13.28.

Isomer B was likewise treated with maleic acid to give after two recrystallizations from EtOAc-Et$_2$O the pure maleate salt of Isomer B: mp 143.5°-145°. IR (nujol); 2660, 2620, 2540, 2480 (N$^+$H, acid OH)cm$^{-1}$, 1695, 1635, 1580, 1470 (C=O, CO$_2{}^-$); mass spec. m/e 400 (M+), 316, 318, 320, ([C$_6$H$_2$Cl$_2$]CH$_2$CONCH$_3$CH$_2$CH$_2$C-OCH$_2$CH$_2$—O, 84 (CH$_2$=CHCH=N(CH$_3$)$_2$). The spectral evidence was consistent with the structure assigned.

Anal. Calcd. for C$_{23}$H$_{30}$Cl$_2$N$_2$O$_7$: C, 53.39; H, 5.84; N, 5.41; Cl, 13.70, Found: C, 53.15; H, 6.08; N, 5.63; Cl, 13.76.

EXAMPLE 7 trans (±) 3,4-Dichloro-N-[7-(dimethylamino)-1,4-dioxaspiro[4.5]-dec-8-yl]benzeneacetamide, (Isomer A), and trans (±) 3,4-Dichloro-N-[8-(dimethylamino)-1,4-dioxaspiro-[4.5]dec-7-yl]benzeneacetamide monohydrochloride (Isomer B) and trans-N$^8$,N$^8$-Dimethyl-1,4-dioxaspiro[4.5]decane-7,8-diamine A. trans-N$^7$, N$^7$-dimethyl-1,4-dioxaspiro[4.5]decane-7,8-diamine and trans-N$^8$,N$^8$-dimethyl-1,4-dioxaspiro[4.5]-decane-7,8-diamine To a solution of 25.0 g (0.125 mol) of the aminoalcohol from Example 5, Part A, and 15.15 g (0.137 mol) of Et$_3$N in 250 ml of CH$_2$Cl$_2$ cooled to 0°, was added dropwise over a period of ca. one hour a solution of 15.7 g (0.137 mol) of methanesulfonyl chloride (Ms-Cl) in 75 ml of CH$_2$Cl$_2$. After the addition was complete the reaction mixture was stirred at 0° for one hour and then distributed between CH$_2$Cl$_2$ and ice H$_2$O. The organic phase was separated, dried (MgSO$_4$) and the solvent removed in vacuo leaving 35.8 g of a light yellow solid.

The light yellow solid crude mesylate was placed in a stainless steel bomb, and 350 ml of liquid ammonia was added and the sealed bomb was heated on a steam bath for sixty hours. (Reaction mixture rapidly built up pressure (900 psi) when first heated. The steam bath was turned off and once the pressure had fallen to 350 psi, heating was resumed.) The excess ammonia was evaporated off in a stream of N$_2$ and the residue was distributed between CH$_2$Cl$_2$ and H$_2$O. The phases were separated, the aqueous phase was extracted with CH$_2$Cl$_2$, the combined organics were dried (MgSO$_4$) and the solvent removed in vacuo leaving 25.4 g of crude product.

The crude product was distilled at reduced pressure through a short path to give 18.5 g (75%) of a mixture of the subtitled diamines: bp 85°-91° C. (0.04 mm).

B. trans-3,4-Dichloro-N-[7-(dimethylamino)-1,4-dioxaspiro[4.5]-dec-8-yl]benzeneacetamide (Isomer A) and trans3,4-Di-chloro-N-[8-(dimethylamino)-1,4-dioxaspiro[4.5]-dec-7-yl]benzeneacetamide monohydrochloride (Isomer B)

To a solution of 4.6 g (20.3 mmol) of the diamine mixture from Part A and 2.5 g (22.4 mmol) of Et$_3$N in 150 ml of dry Et$_2$O was added dropwise over a ca. 0.75 hour period a solution of 5.0 g (22.4 mmol) of 3,4-dichlorophenylacetyl chloride in 50 ml of dry Et$_2$O. After the addition was complete the reaction mixture was stirred at ambient temperature for four hours and then distributed between EtOAc and H$_2$O. The aqueous phase was extracted with EtOAc and the combined organics were washed with brine, dried (MgSO$_4$) and the solvent removed in vacuo, leaving 8.0 g of crude amide as a yellow oil.

A 3.0 g aliquot of the crude amide product was chromatographed on silica gel (Merck Lobar column) eluting with NH$_3$:MeOH:EtOAc,0.5:4.5:95 (v:v), to give 0.5 g of pure titled Isomer A, 0.9 g of the pure titled Isomer B and mixed fraction. The chromatographically pure Isomer A (a glass) was dissolved in a minimum volume of boiling EtOAc and the resulting solution stored at 0° C. The crystals were collected and recrystallized from EtOAc to give the pure titled Isomer A: mp 176°-178° C.; IR (nujol) 3300, 3070 (NH) cm$^{-1}$, 2780 (N—C—H), 1635 (C=O), 1550 (amide II); mass spec. m/e 386,388 (M+), 142 ((CH$_3$)$_2$N$^+$=CH$_2$CH=C-OCH$_{22}$CH$_2$O). The spectral evidence was consistent with the structure assigned.

Anal. Calcd. for C$_{18}$H$_{24}$Cl$_2$N$_2$O$_3$: C, 55.81; H, 6.24; N, 7.23; Cl, 18.31, Found: C, 55.94; H, 6.44; N, 7.39; Cl, 18.21.

An ethereal solution of Isomer B was treated with ethereal HCl and the resultant hygroscopic precipitate was collected and recrystallized twice from EtOAc-Et$_2$O to give the monohydrochloride of Isomer B: mp 204°-208° (dec); IR (nujol), 3240, 3200, 3060 (NH) cm$^{-1}$, 2580, 2520, 2480, 2440, (NH), 1670 (C=O), 1560 (amide II); mass spec., m/e 386,388,390 (M+), 84 ((CH$_3$)$_2$N=CHCH=CH$_2$). The spectral evidence was consistent with the structure assigned.

Anal. Calcd. for C$_{18}$H$_{25}$Cl$_3$N$_2$O$_3$: C, 51.01; H, 5.95; N, 6.61; Cl, 25.10, Found: C, 50.74; H, 6.23; N, 6.68; Cl, 25.28.

EXAMPLE 8 trans (±) 4-Bromo-N-[7-(dimethylamino)-1,4-dioxaspiro[4.5]dec-8-yl]benzamide (Isomer A) and trans (±) 4-Bromo-N-[8-(dimethylamino)-1,4-dioxaspiro[4.5]-dec-7-yl]benzamide (Isomer B)

To a solution of 5.0 g (25 mmol) of the diamine mixture from Example 7, Part A and 2.9 g (26 mmol) of Et$_3$N in 150 ml of dry Et$_2$O was added dropwise over a period of ca. one hour a solution of 5.8 g (26.2 mmol) of 4-bromobenzoyl chloride in 50 ml of Et$_2$O. After the addition was complete the reaction mixture was stirred at ambient temperature for three hours and then distributed between EtOAc and H$_2$O. The aqueous phase was extracted twice with EtOAc. The combined organics were washed with brine, dried (MgSO$_4$) and the solvent removed in vacuo leaving 9.0 g of crude amide as a yellow solid.

The crude amide product was dissolved in a minimum volume of boiling EtOAc and cooled and the resultant crystals were collected and recrystallized twice from EtOAc to give 1.8 g of the pure titled Isomer B: mp 178°–180° C.; IR (nujol) 3340, 3320(NH)cm$^{-1}$, 2780 (N—C—H), 1630 (C=O), 1595, 1485 (C=C), 1550 (amide II); mass spec., m/e 382,384 (M+), 84 ((CH$_3$)$_2$N$^+$=CHCH=CH$_2$). The spectral evidence was consistent with the structure assigned.

Anal. Calcd. for C$_{17}$H$_{23}$BrN$_2$O$_3$: C, 53.27; H, 6.05; N, 7.31; Br, 20.85, Found: C, 53.34; H, 6.24; N, 7.27; Br, 20.54.

A 3 g portion of the mother liquors was chromatographed on silica gel (Merck Lobar column) eluting with NH$_3$:MeOH:EtOAc, 0.5:4.5:95 (v:v), to give 0.8 g of pure titled Isomer A (oil) as well as mixed fractions. The oil thus obtained was dissolved in EtOAc and stored at 0° C. The crystals which separated were collected and recrystallized from EtOAc-Et$_2$O to give the pure titled Isomer A: mp 184°–187° (dec); IR (nujol), 3320 (NH) cm$^{-1}$, 2770 (N—C—H), 1635 (C=O), 1540 (amide II); mass spec. m/e 382,384 (M+), 142 ((CH$_3$)$_2$NCH=CHC=O—CH$_2$CH$_2$O). The spectral evidence was consistent with the structure assigned.

Anal. Calcd. for C$_{17}$H$_{23}$BrN$_2$O$_3$:C, 53.27; H, 6.05; N, 7.31; Br, 20.85, Found: C, 53.06; H, 5.97; N, 7.26; Br, 20.58.

EXAMPLE 9 trans-4-Bromo-N-methyl-N-[8-(1-pyrrolidinyl)-1,4-dioxaspiro[4.5]dec-7-yl]benzamide, (Isomer B) and trans-4-bromo-N-methyl-N-[7-(1-pyrrolidinyl)-1,4-dioxaspiro[4.5]dec-8-yl]benzamide, (Isomer A)

A mixture of isomeric diamines (2.96 g, 0.013 mol) from Example 1, Part G, triethylamine (1.59 g, 0.016 mol), and 80 ml of anhydrous Et$_2$O was stirred while a solution of 4-bromobenzoyl chloride (3.45 g, 0.016 mol) in 20 ml of Et$_2$O was added dropwise. The mixture was stirred for three hours after the addition was completed. The mixture was diluted with chloroform and made basic by addition of 50 ml of 10% sodium hydroxide solution. The organic layer was separated and the aqueous layer was again extracted with chloroform. The combined organic layers were washed with brine, dried (Na$_2$SO$_4$), and concentrated on a rotary evaporator to dryness. The residue weighed 7.3 g. The residue was chromatographed over 300 g. of E. Merck Company silica gel with 12 l of Et$_3$N:EtOAc:hexane (1:25:74,v/v) at medium pressure. A 2.0 l fore-run was discarded and fractions were collected in 18 ml quantities. The titled Isomer A eluted in fractions 209–246, crystals from hexane, 1.3 g (23.4%), mp 142.8°–157.7° C. Mass spectrum, m/e 209 (M+—CH$_3$NH-COC$_6$—H$_5$Br; nmr and ir were consistent with the structure assignment.

Anal. Calcd. for C$_{20}$H$_{27}$BrN$_2$O$_3$: C, 56.74; H, 6.43; Br, 18.88; N, 6.62, Found: C, 56.78; H, 6.70; Br, 18.72; N, 6.57.

The pure titled Isomer B eluted in fractions 270–390, crystals from EtOAc-hexane, 1.5 g (27%), mp 112.2°–113.5° C. Mass spectrum, m/e 422/425 (M+, bromine isotopic peaks); NMR and IR were compatible with the structure assignment.

Anal. Calcd. for C$_{20}$H$_{27}$BrN$_2$O$_3$: C, 56.74; H, 6.43; Br, 18.88; N, 6.62, Found: C, 56.83; H, 6.80; Br, 18.72; N, 6.52.

EXAMPLE 10 trans-3,4-Dichloro-N-methyl-N-[7-[methyl(2-propenyl)amino]-1,4-dioxaspiro[4.5]dec-8-yl]benzeneacetamide 4-methylbenzene sulfonate, hemihydrate and trans-3,4-dichloro-N-methyl-N-[8-[methyl(2-propenyl)amino]-1,4-dioxaspiro[4.5]dec-7-yl]benzeneacetamide

A.

trans-±-7-[methyl(2-propenyl)amino]-1,4-dioxaspiro[4.5]decane-8-ol

A solution of 20.3 g (0.13 mol) of spiro[7-oxabicyclo[4.1.0]heptane-3,2′-[1,3]-dioxolane] from Example 1, Part D, in 20 ml allylmethylamine and 8 ml H$_2$O was heated to 85° for eighteen hours. The mixture was concentrated in vacuo and the residue distributed between EtOAc and 30% NaOH. The organic phase was separated, dried (MgSO$_4$) and concentrated in vacuo. The residue was vacuum distilled to give 26.4 g, bp 99° (0.02 mm) (89%) of the subtitled amino alcohol. Nmr (CDCl$_3$), δ5.5–6.1 (m, 1H, CH=CH$_2$), 6.5–5.3 (m, 2H, CH=CH$_2$), 4.63 (s, 4H, CH$_2$O), δ2.5–3.75 (m, 4H, CH—O, CH—N, CH$_2$—CH), 2.25 (s, 3H, N-CH$_3$), 1–2 (m, 6H, ring CH$_2$); IR (nujol); 3460 (OH) cm$^{-1}$, 3080 (=CH), 2800 (N—C—H), 1645 (C=C), 1145, 1080, 1035 (C=O, other); mass spec., m/e 227 (M+), 200 (M+—CH=CH$_2$), 168 (CH$_2$=CH—CH$_2$N(CH$_3$)CH=CH—C=O$_+$—CH$_2$C-H$_2$O). The spectral evidence was consistent with the structure assigned.

Anal. Calcd. for C$_{12}$H$_{21}$NO$_3$: C, 63.41; H, 9.31; N, 6.16, Found: C, 63.61; H, 9.56; N, 6.16.

B.

trans-±-N$^7$,N$^8$-dimethyl-N$^7$-(2-propenyl)-1,4-dioxospiro[4.5]decane-7,8-diamine and trans-±-N$^7$,N$^8$-dimethyl-N$^8$-(2-propenyl)-1,4-dioxaspiro[4.5]decane7,8-diamine An ice cold solution of 15.0 g (0.066 mol) of trans-(±3)-N-[8-hydroxy-1,4-dioxaspiro[4.5]dec-7-yl]-N-methyl-N-(2-propenyl)amine from Part A and 8.01 g (0.0792 mol) of Et$_3$N in 250 ml CH$_2$Cl$_2$ was treated with 9.07 g (0.0792 mol) of methanesulfonyl chloride over 10 minutes. After one hour, the solution was added to 250 ml H$_2$O and the organic phase separated, dried (MsSO$_4$) and concentrated in vacuo at ambient temperature. The crude mesylate was mixed with 100 ml 40% aqueous methylamine with ice bath cooling. After fifteen minutes the solution was allowed to warm to ambient temperature and then heated to 70° for three hours. The mixture was cooled and distributed between H$_2$O and CH$_2$Cl$_2$. The organic phase was separated and the aqueous phase treated with solid NaOH and extracted with CH$_2$Cl$_2$. The combined organic phases were dried (MgSO$_4$) and concentrated in vacuo to give 15.5 g (98%) of crude diamine. The product was vacuum distilled to give 13.7 g (86%) of a mixture of the titled diamines: bp 88–94 (0.02 mm), nmr (CDI$_3$), δ5.5–6.0 (m, 1H, CH=CH$_2$), 4.9–5.3 (M, 2H, CH=CH$_2$), δ3.94, δ3.92 (S for each isomer, 4H, (CH$_2$)$_2$O), 2.5–3.2 (M, 5H), 2.40, 2.37 (S for each isomer, 3H, N—CH$_3$), 2.16, 2.13 (S for each isomer, 3H, N—CH$_3$); IR (nujol), 3580, 3320 (NH), 2780 (N—C—H), 1645 C=C). The spectral evidence was consistent with the structures assigned.

C.

trans-(±)-3,4-Dichloro-N-methyl-N-[7-]methyl(2-propenyl)-amino]-1,4-dioxaspiro[4.5]dec-8-yl]benzeneacetamide 4-methylbenzenesulfonate hemihydrate (Isomer A) and
trans-(±)-3,4-dichloro-N-methyl-N-[8-[methyl(2-propenyl)amino]-1,4-dioxaspiro[4.5]dec-7-yl]-benzeneacetamide A solution of 6.0 g (0.025 mol) of a mixture of diamines from Part B and 3.0 g (0.03 mol) of Et$_3$N in 250 Et$_2$O was treated with 6.7 g (0.03 mol) of 3,4-dichlorophenylacetyl chloride in 250 ml of Et$_2$O over thirty minutes. After one and one-half hours the mixture was filtered and the filtrate washed with H$_2$O, 10% NaOH, H$_2$O, brine, dried (MgSO$_4$) and concentrated in vacuo leaving 10.5 g (100%) of a mixture of isomers as an oil.

A chromatography of 1 g of the crude oil on 150 g silica gel eluting with MeOH-NH$_3$-Et$_2$O, 1.95:0.05:98 (v/v), gave 0.11 g of the titled Isomer A and 0.5 g of mixed fractions. A second chromatography with 2 g of oil on 3 (E Merck Company) size B silica gel columns eluting with MeOH-hexane-EtOAc, 1.5:49.25:49.25 (v/v), gave 0.2 g of the titled Isomer A and 1.5 g of mixed fractions. The combined fractions of pure Isomer A were treated with one equivalent of p-toluenesulfonic acid hydrate in MeOH/EtOAc to give a salt. The salt was recrystallized twice from MeOH-EtOAc to give 0.25 g of the titled amino-amide salt: mp 127°–128° C.

Anal. Calcd. for $C_{28}H_{36}Cl_2N_2SO_6$·0.5 H$_2$O: C, 55.26; H, 6.13; Cl, 11.65; N, 4.60; S, 5.27, Found: C, 55.64; H, 5.94; Cl, 11.29; N, 4.39; S, 5.23.

EXAMPLE 11 trans-3,4-Dichloro-N-[5-(hydroxyimino)-2-(1-pyrrolidinyl)-cyclohexyl]-N-methylbenzeneacetamide A mixture of the ketone from Example 4, Part A (2.1 g, 0.005 mol), hydroxylamine hydrochloride (0.54 g; 0.0078 mol), 95% ethanol (10 ml), and water (5 ml) was stirred at room temperature while crushed sodium hydroxide (1.0 g, 0.025 mol) was added portionwise. When the addition was completed the mixture was rapidly heated to reflux temperature and stirred for about five minutes. Hydrochloric acid solution (1 N) was added dropwise until the mixture became cloudy. Stirring was continued for about five minutes longer before white solid separated from the mixture. The solid was filtered, washed with a large volume of water and dried to give 1.3 g (65%) of the title oxime. Similarly the filtrate yielded a second crop, 0.2 g (10%), or 1.5 g total of the titled oxime, mp 115°–117.5° C. Mass spectrum m/e 397 (M+). Nmr and ir spectra were consistent with the structure assignment.

Anal. Calcd. for $C_{19}H_{25}Cl_2N_3O_2$: C, 57.29; H, 6.33; Cl, 17.80; N, 10.55, Found: C, 57.04; H, 6.39; Cl, 18.11; N, 10.42.

EXAMPLE 12

Part A.

trans-7-[N-Methylamino]-8-(1-piperidinyl)-1,4-dioxaspiro[4.5]decane and
trans-8-(N-methylamino)-7-(1-piperidinyl)-1,4-dioxaspiro[4.5]decane Method A: The aziridine of Example 1, Part F, is reacted with piperidine as described in Example 1, Part G, Method A, to produce a mixture of the titled diamines.

Method B: The hydroxy compound of Example 1, Part E, is reacted with methanesulfonyl chloride followed by reaction of this sulfonate ester with piperidine as described in Example 1, Part G, Method B, to yield a mixture of the titled diamines.

Part B. trans-3,4-dichloro-N-methyl-N-[7-(1-piperidinyl)-1,4-dioxaspiro[4.5]dec-8-yl]benzeneacetamide (Isomer A) and trans-3,4-dichloro-N-methyl-N-[8-(1-piperidinyl)-1,4-dioxaspiro[4.5]dec-7-yl]benzeneacetamide (Isomer B)

A mixture of the diamines from Part A is reacted as described in Example 1, Part H, to afford the titled amides: Isomer A, mp 174°–177° C. and Isomer B.

EXAMPLE 13 trans-4-bromo-N-methyl-N-[7-(1-piperidinyl)-1,4-dioxaspiro-[4.5]dec-8-yl]benzamide (Isomer A) and
trans-4-bromo-N-methyl-N-(8-(1-piperidinyl)-1,4-dioxaspiro[4.5]dec-7-yl]benzamide (Isomer B)

A mixture of diamines from Example 12, Part A, is reacted as described in Example 9 to yield the titled amides: Isomer A, mp 130°–132° C. and Isomer B, mp 194°–194.5° C.

EXAMPLE 14 trans-±-3,4-dichloro-N-methyl-N-[8-(1-pyrrolidinyl)-1-oxa-4-thiaspiro[4.5]dec-7-yl]benzeneacetamide and its monohydrochloride hydrate Sufficient ketone hydrochloride from Example 4A above was reacted with 2 N sodium hydroxide, and the ketone free base was extracted into chloroform, which was evaporated to give 5.0 g (0.013 mole) of free base. To this ketone free base dissolved in toluene (150 ml) was added 2-mercaptoethanol (5 ml, 5.5 g, 0.071 mole) and 3.0 g (0.016 mole) of p-toluenesulfonic acid monohydrate, and the mixture was refluxed with removal of the water formed using a Dean Stark trap until TLC indicated substantial disappearance of starting material. The crude product was concentrated and then chromatographed on 260 g of silica gel eluting with 1% ammonium hydroxide in methylene chloride. Three of the fractions obtained afforded 0.95 g (not the total yield) of free base, which was dissolved in chloroform. This solution was treated with decolorizing carbon, and then HCl in diethyl ether was added to produce the hydrochloride salt. Recrystallization of this salt from chloroform-diethyl ether afforded the titled compound as a partial hydrate, mp 220–226 (when the sample tube was placed in a bath at 200° and the temperature was increased one degree per minute).

EXAMPLE 15

(1α,2β,4β)-N-[(4-(acetyloxy)-2-(1-pyrrolidinyl)cyclohexyl]-3,4-dichloro-N-methylbenzeneacetamide and its monohydrochloride

A.

(1α,2β,4β)-3,4-dichloro-N-[4-hydroxy-2-(1-pyrrolidinyl)cyclohexy]-N-methylbenzeneacetamide and its monohydrochloride hydrate To trans-3,4-dichloro-N-methyl-N-[4-oxo-2-(1-pyrrolidinyl)-cyclohexyl]benzeneacetamide hydrochloride (described in Example 2 above) (5.0 g, 0.012 mole) in 100 ml of absolute ethanol at ambient temperature (20°–25° C.) was added in portions 1.2 g (0.032 mole) of sodium borohydride. The mixture was stirred overnight at ambient temperature and then diluted with water (100 ml) and extracted three times with chloroform (150 ml portions). The combined organic layers were dried (Na2SO4) and concentrated to an oil, which was dissolved in chloroform and reacted with HCl in diethyl ether. The solid was filtered and recrystallized from chloroform-ethylacetate-diethyl ether to give 2.6 g (51%) and 0.3 g (6) of the subtitled alcohol, mp 125°–239° C. (dec). Mass spec (m/e 383,385, M+, chlorine isotopic peaks), nmr and UV spectral analyses were consistent with the structure assigned.

B.

(1α,2β,4β)-N-[(4-acetyloxy)-2-(1-pyrrolidinyl)cyclohexyl]-3.4-dichloro-N-methylbenzeneacetamide and its monohydrochloride The (1α,2β,4β)-alcohol from Part A above was reacted with acetic anhydride in pyridine and chloroform by the method described above in Example 4C to give the titled acetate as the monohydrochloride, mp 150–161.5 C.

Examples 16, 17, 18 and 19 describe the use of two different nitrogen protecting groups, benzyl and tert-butyloxycarbonyl, the benzyl group being removed (by hydrogenolysis) in the presence of the tert-butyloxycarbonyl group, which is then removed in a later step.

EXAMPLE 16 trans-(±)-N-(7-amino-1,4-dioxaspiro[4.5]dec-8-yl)-3,4-dichloro-N-methylbenzeneacetamide and its trifluoroacetate salt

A.

trans-(±)-8-hydroxy-N-methyl-N-(phenylmethyl)-1,4-dioxaspiro[4.5]decan-7-amine

Spiro[7-oxabicyclo[4.1.0]heptane-3,2'-[1,3]dioxolane]-(prepared as described in Example 1D above) is reacted with methyl(phenylmethyl)amine by a procedure analogous to that of Example 1E above to give an 89% yield of the subtitled amino alcohol, bp 174°–176° C. (0.02 mm Hg).

B.

trans-(±)-N7-methyl-N7-(phenylmethyl)-1,4-dioxaspiro[4.5]decane-7,8-diamine and
trans-(±)-N8-methyl-N8-(phenylmethyl)-1,4-dioxaspiro[4.5]decane-7,8-diamine The amino alcohol from Part A above is reacted with methanesulfonyl chloride by the method of Example 5B above, and the resulting methanesulfonate ester is reacted with anhydrous ammonia at 60° by the method of Example 5B above to give an approximately 1:1 mixture (by nmr) of the subtitled diamines.

C.

trans-(±)-[8-[methyl(phenylmethyl)amino]-1,4-dioxaspiro[4.5]dec-7-yl]carbamic acid, 1,1-dimethylethyl ester (Isomer A) and
trans-(±)-[7-[methyl(phenylmethyl)amino]-1,4-dioxaspiro[4.5]dec-8-yl]carbamicacid, 1,1-dimethylethyl ester (Isomer B)

The mixture of diamines from Part B above is reacted with 2-(tert-butoxycarbonyloxyimino)-2-phenylacetonitrile in tetrahydrofuran at 65° to form a mixture of the subtitled doubly nitrogen-protected diamines, which are separated by silica gel chromatography to give Isomer A as an oil and Isomer B as a solid, mp 106°–108° C.

D.

trans-(±)-[8-[[(3,4-dichlorophenyl)acetyl]methylamino]-1,4-dioxaspiro[4.5]dec-7-yl]carbamic acid, 1,1-dimethylethyl ester The 8-[methyl(phenylmethyl)amino] compound (Isomer A) from Part C above is hydrogenated using palladium on carbon as a catalyst to remove the benzyl group from the nitrogen atom attached to carbon atom number eight and this same nitrogen is then acylated using 3,4-dichlorophenylacetyl imidazolide (from 3,4-dichlorophenylacetic acid and N,N'-carbonyldiimidazole) to give the subtitled protected-amino amide, mp 145°–147° C.

E.

trans-(±)-N-(7-amino-1,4-dioxaspiro[4.5]dec-8-yl)-3,4-dichloro-N-methylbenzeneacetamide and its trifluoroacetate salt The tert-butyloxycarbonyl-protected compound from Part D above is reacted with trifluoroacetic acid in methylene chloride solution at 0° C. for fifteen minutes so as to remove the tert-butyloxycarbonyl (but not the ketal) group and afford the titled amino amide which is isolated as the trifluoroacetate salt, mp 188°–191° C.

Anal. Calcd. for $C_{17}H_{22}Cl_2O_3CF_3CO_2H$: C, 46.83; H, 4.76; N, 5.75; Cl, 14.55, Found: C, 46.80; H, 4.90; N, 5.91; Cl, 14.69.

EXAMPLE 17 trans-(±)-N-(8-amino-1,4-dioxaspiro[4.5]dec-7-yl)-3,4-dichloro-N-methylbenzeneacetamide and its trifluoroacetate salt

A.

trans-(±)-[7-[[(3,4-dichlorophenyl)acetyl]methylamino]-1,4-dioxaspiro[4.5]dec-8-yl]carbamic acid, 1,1-dimethylethyl ester By methods analogous to those described in Example 16D above, the 7-[methyl(phenylmethyl)amino] compound (Isomer B) from Example 16C above is converted to the subtitled protected-amino amide, mp 212.5°–2.14° C.

B.

trans-(±)-N-(8-amino-1,4-dioxaspiro[4.5]dec-7-yl)-3,4-dichloro-N-methylbenzeneacetamide and its trifluoroacetate salt The tert-butyloxycarbonyl-protected-amino amide from Part A above is reacted with trifluoroacetic acid in methylene chloride solution at approximately 0° C. for a time sufficient to produce the titled amino amide which is isolated as the trifluoroacetate salt.

Treatment of this trifluoroacetate salt with a base such as sodium hydroxide or sodium bicarbonate generates the titled free base, which is reacted with a desired acid to produce the corresponding acid addition salt of the titled free base.

EXAMPLE 18 trans-(±)-3,4-dichloro-N-methyl-N-[7-(methylamino)1,4-dioxaspiro[4.5]dec-8-yl]benzeneacetamide and its monohydrochloride

A.

trans-(±)-N7,N8-dimethyl-N7-(phenylmethyl)-1,4-dioxospiro[4.5]decane-7,8-diamine and trans-(±)-N7,N8-dimethyl-N8-(phenylmethyl)-1,4-dioxaspiro[4.5]decane-7,8-diamine The amino alcohol of Example 16A above is reacted with methanesulfonyl chloride by the method of Example 5B above, and the resulting methanesulfonate ester is reacted with aqueous methylamine at 90° C. to produce a 75% yield of a mixture of the subtitled diamines, bp 152°–158° C. (0.05 mm).

B.

trans-(±)-N-methyl-[8-[methyl(phenylmethyl)amino]1,4-dioxaspiro[4.5]dec-7-yl]carbamic acid, 1,1-dimethylethyl ester (Isomer A) and trans-(±)-N-methyl[7-[methyl(phenylmethyl)amino]-1,4-dioxaspiro[4.5]-dec-8-yl]carbamic acid, 1,1-dimethylethyl ester (Isomer B)

The mixture of diamines from Part A above is reacted with 2-(tert-butoxycarbonyloxyimino)-2-phenylacetonitrile in tetrahydrofuran at 65° to form a mixture of the subtitled doubly nitrogen-protected diamines, which are separated by silica gel chromatography to afford pure Isomer A and pure Isomer B.

C.

trans-(±)-[8-[[(3,4-dichlorophenyl)acetyl]methylamino]-1,4-dioxaspiro[4.5]dec-7-yl]-N-methylcarbamic acid, 1,1-dimethylethyl ester The 8-[methyl(phenylmethyl)amino] compound (Isomer A) from Part B above is hydrogenated using palladium on carbon as a catalyst to remove the benzyl group from the nitrogen atom attached to carbon atom number eight and this same nitrogen is then acylated using 3,4-dichlorophenylacetyl imidazolide (from 3,4-dichlorophenylacetic acid and N,N'-carbonyldiimidazole) to give the subtitled protected-amino amide, mp 121°–123° C.

D.

trans-(±)-3,4-dichloro-N-methyl-N-[7-(methylamino)1,4-dioxaspiro[4.5]dec-8-yl]benzeneacetamide and its monohydrochloride The tert-butyloxycarbonyl-protected compound from Part C above is reacted with trifluoroacetic acid in methylene chloride solution at 0° C. for fifteen minutes so as to remove the tert-butyloxycarbonyl (but not the ketal) group. The mixture is made basic with sodium hydroxide, and the titled free base is reacted with Et$_2$O/HCl to give the titled amino amide salt, mp 238°–240° C.

Anal. Calcd. for $C_{18}H_{24}Cl_2N_2O_3$·HCl: C, 51.02; H, 5.95; N, 6.61; Cl, 25.10, Found: C, 50.50; H, 5,88; N, 6.42; Cl, 24.93.

EXAMPLE 19 trans-(±)-3,4-dichloro-N-methyl-N-[8-(methylamino)-1,4-dioxaspiro[4.5]dec-7-yl]benzeneacetamide and its monohydrochloride

A.

trans-(±)-[7[[(3,4-dichlorophenyl)acetyl]methylamino]-1,4-dioxaspiro[4.5]dec-8-yl]-N-methylcarbamic acid, 1,1-dimethylethyl ester By methods analogous to those described in Example 18C above the 7-[methyl(phenylmethyl)amino] compound (Isomer B) from Example 18B above is converted to the subtitled protected-amino amide, mp 160°–161° C.

B.

trans-(±)-3,4-dichloro-N-methyl-N-[8-(methylamino)-1,4-dioxaspiro]4.5]dec-7-yl]benzeneacetamide and its monohydrichloride The tert-butyloxycarbonyl-protected-amino amide from Part A above is reacted with trifluoroacetic acid in methylene chloride solution at 0° C. for fifteen minutes so as to remove the tert-butyloxycarbonyl (but not the ketal) group. The mixture is made basic with sodium bicarbonate, and the titled free base is reacted with Et$^2$O/HCl to give the titled amino amide salt, mp 206°–207° C.

Anal. Calcd. for $C_{18}H_{24}Cl_2N_2O_3$·HCl: C, 51.02; H, 5.95; N, 6.61; Cl, 25.10, Found: C, 51.12; H, 5.94; N, 6.72; Cl, 24.44.

Other representative examples of compounds within the scope of this invention which can be prepared by procedures described in this specification are the cis and trans isomers of:

a. N-methyl-N-[7-(1-pyrrolidinyl)-1,4-dioxaspiro[4.5]dec-8-yl]-4-trifluoro-methylbenzeneacetamide b. N-methyl-N-[8-(1-pyrrolidinyl)-1,4-dioxaspiro[4.4]non-7-yl]-3-trifluoro-methylbenzeneacetamide c. 4-chloro-N-methyl-N-[7-(1-pyrrolidinyl)-1,4-dioxaspiro[4.5]-dec-8-yl]-benzamide d. 4-fluoro-N-methyl-N-[7-(1-pyrrolidinyl)-1,4-dioxaspiro[4.6]-undec-8-yl]-benzamide e. 4-Bromo-N-methyl-N-[9-(1-piperidinyl)-1,4-dioxaspiro[4.6]-undec-8-yl]-benzeneacetamide f. N-[8-(1-azetidinyl)-1,4-dioxaspiro[4.5]-dec-7-yl]-N-methyl-4-nitrobenzamide g. N-(8-amino-1,4-dioxaspiro[4.6]-undec-7-yl)-N-methyl-2-chlorobenzenacetamide h. 3-amino-N-methyl-N-[8-(1-pyrrolidinyl)-1,4-dioxaspiro[4.5]-dec-7-yl]-benzeneacetamide i. N-[8-(ethylamino)-1,4-dioxaspiro[4.4]non-7-yl]-4-methoxy-N-methylbenzamide j. 3-hydroxy-N-[7-(isopropylamino)-1,4-dioxaspiro[4.5]-dec-8-yl]-N-methylbenzeneacetamide k. (4R)- or (4S)-N-[2-(allylmethylamino)-4-(propionyloxy)cyclohexyl]-4-azido-N-methylbenzamide l. N-[7-(diethylamino)-1,4-dioxaspiro[4.5]dec-8-yl]-N,2-dimethyl-benzeneacetamide m. N-[8-(1-azetidinyl)-1,4-dithiaspiro[4.5]dec-7-yl]-N-methyl[1,1'biphenyl]-3-acetamide n. N-[8-(dimethylamino)-1,4-dioxaspiro[4.5]dec-7-yl]-3-methanesulfonyl-N-methylbenzamide o. N-[4-(acetyloxyimino)-2-(di-n-propylamino)cyclopentyl]-2-cyano-N-ethylbenzamide p. 3-ethoxycarbonyl-N-methyl-N-[9-(1-piperidinyl)-1,4-dioxaspiro[4.6]-undec-8-yl]benzamide p1 q. 4-acetyloxy-N-[2-(1-azetidinyl)-6-thioxocycloheptyl]-N-methylbenzamide
r. (4R)- or (4S)-4-bromo-N-[4-methoxy-2-(1-pyrrolidinyl)cyclopentyl]-methylbenzamide
s. (5R)- or (5S)-N-[9-(1-azetidinyl)-5-ethoxycycloheptyl]-3,4-dichloro-N-ethylbenzeneacetamide
t. 3,4-dibromo-[2-(dimethylamino)-4-oxocycloheptyl]-N-methylbenzene-acetamide
u. 4-chloro-N-methyl-[4-oxo-2-(1-piperidinyl)cyclopentyl]-benzamide
v. 3,4-dichloro-N-ethyl-N-[8-(1-pyrrolidinyl)-1,4-dioxaspiro[4.4]non-7-yl]benzeneethanethioamide
w. 4-bromo-N-methyl-N-[8-(1-pyrrolidinyl)-1,4-dioxaspiro[4.4]-non-7-yl]-benzenecarbothioamide
x. 3,4-dichloro-N-methyl-N-[7-(1-pyrrolidinyl)]-1,4-dioxaspiro-[4.5]-dec-8-yl]-benzeneethanethioamide
y. 4-bromo-4-methyl-N-[7-(1-pyrrolidinyl)-1,4-dioxaspiro[4.5]-dec-8-yl]-benzenecarbothioamide
z. 3,4-dichloro-N-methyl-N-[8-(1-pyrrolidinyl)-1,4-dioxaspiro-[4.5]dec-7-yl]:benzeneethanethioamide
aa. 4-bromo-N-methyl-N-[8-(1-pyrrolidinyl)-1,4-dioxaspiro[4.5]-dec-7-yl]-benzenecarbothioamide
bb. 3,4-dichloro-N-methyl-N-[7-(1-pyrrolidinyl)-1,4-dioxaspiro[4.6]-undec-8-yl]benzeneethane-thioamide
cc. 3,4-dichloro-N-(1-n-propyl)-N-[9-(1-pyrrolidinyl)-1,4-dioxaspiro-[4.6]-undec-8-yl]benzeneethanethioamide
dd. 3,4-dichloro-N-methyl-N-[8-(1-pyrrolidinyl)-1,4-dioxaspiro[4.6]-undec-7-yl]benzeneethanethioamide
ee. 4-bromo-N-methyl-N-[7-(1-pyrrolidinyl)-1,4-dioxaspiro[4.6]undec-8-yl]-benzenecarbothioamide
ff. 4-bromo-N-methyl-N-[9-(1-pyrrolidinyl)-1,4-dioxaspiro[4.6]undec-8-yl]-benzenecarbothioamide
gg. 4-bromo-N-ethyl-N-[8-(1-pyrrolidinyl)-1,4-dioxaspiro[4.6]undec-7-yl]-benzenecarbothioamide
hh. N-[5-(acetyloxyimino)-2-(1-pyrrolidinyl)cyclohexyl]3,4-dichloro-N-methylbenzeneacetamide
ii. 3,4-dichloro-N-[4-(hydroxyimino)-2-(1-pyrrolidinyl)cyclohexyl]-N-methylbenzeneacetamide
jj. N-[4-(acetyloxyimino)-2-(1-pyrrolidinyl)cyclohexyl]benzeneacetamide

We claim:
1. A compound of the formula

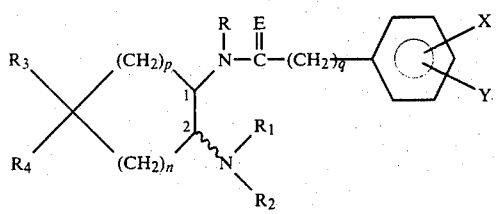

wherein p and n are each full number integers of from 1 to 3, so that the resulting cycloaliphatic ring has five to seven carbon atoms; the wavy line bond (~) between the nitrogen in the 2-position and the cycloaliphatic ring carbon indicates the bond can be either cis- or trans- with respect to each substituent on the cycloaliphatic ring;
q is 0 or 1;
X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino [(-NHC(O)$R_6$)];
R is hydrogen or $C_1$ to $C_3$-alkyl;
$R_1$ and $R_2$, taken separately, are hydrogen, $C_1$ to $C_3$-alkyl, allyl,
$R_1$ and $R_2$, taken together with the nitrogen to which they are bonded, complete a ring selected from the group consisting of azetidinyl, pyrrolidinyl, and piperidinyl;
$R_3$, taken separately, is hydrogen, hydroxy, —$OR_5$ or OC(=O)$R_6$;
$R_4$, taken separately, is hydrogen;
$R_3$ and $R_4$, taken together, are selected from the group consisting of —E$CH_2CH_2$E—;
=E,
[—N~OH], =N~OH and
[-N~OC(O)$CH_3$]=N~OC(O)$CH_3$;
wherein each E is bivalent sulfur or oxygen, and $R_3$ and $R_4$ cannot both be hydrogen at the same time;
$R_5$ is $C_1$ to $C_3$-alkyl;
$R_6$ is hydrogen or $C_1$ to $C_2$-alkyl;
or an acid addition salt thereof, provided that when R is methyl, $R_1$ and $R_2$, taken together with the nitrogen to which they are bonded, form a pyrrolidinyl, X and Y are each chlorine in the 3- and 4-positions of the phenyl ring, p is 1, n is 2, q is 1, E is oxygen, $R_4$ is hydrogen, then $R_3$ cannot be acetoxy and a 5-alpha orientation (on the same side of the cycloaliphatic ring as the amide nitrogen).

2. A compound according to claim 1 wherein p is 1 to 3, n is 1 to 3, q is 0 or 1;
at least one of X and Y is a halogen having an atomic number of from 9 to 35 in the 3- or 4-position of the phenyl ring, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl or piperidinyl group;
$R_3$ and $R_4$ are taken together to form the ring group —E$CH_2CH_2$E—, and each E is oxygen;
or a pharmacologically acceptable salt thereof.

3. A compound according to claim 2 which is trans-3,4-dichloro-N-methyl-N-[8-(1-pyrrolidinyl)-1,4-dioxaspiro[4.5]dec-7-yl]benzeneacetamide, or a pharmacologically acceptable salt thereof.

4. A compound according to claim 2 which is trans-3,4-dichloro-N-methyl-N-[7-(1-pyrrolidinyl)-1,4-dioxaspiro[4.5]dec-8-yl]benzeneacetamide, or a pharmacologically acceptable salt thereof.

5. A compound according to claim 1 wherein p is 1 to 3; n is 1 to 3;
q is 0 or 1;
at least one of X and Y is a halogen having an atomic number of from 9 to 35 in the 3- or 4-position, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl, or piperidinyl ring;
$R_3$ and $R_4$ are taken together to form an =E substituent;
E is oxygen;
or a pharmacologically acceptable salt thereof.

6. A compound of claim 5 which is trans-3,4-dichloro-N-methyl-N-[4-oxo-2-(1-pyrrolidinyl)cyclohexyl]benzeneacetamide, or a pharmaclogically acceptable salt thereof.

7. A compound according to claim 1 wherein p is 1 to 3; n is 1 to 3;
q is 0 or 1;
at least one of X and Y is a halogen having an atomic number of from 9 to 35 in the 3- or 4-position, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl or piperidinyl ring;
$R_3$ is hydrogen and $R_4$ is acetoxy;
E is oxygen;
or a pharmacologically acceptable salt thereof.

8. A compound of claim 7 which is $(1\beta,2\beta,4\alpha)$-3,4-dichloro-N-methyl-N-[4-(acetyloxy)-2-(1-pyrrolidinyl)cyclohexyl]benzeneacetamide, or a pharmacologically acceptable salt thereof.

9. A compound of claim 1 wherein p is 1 to 3; n is 1 to 3;
q is 0 or 1;
each of X and Y is a halogen having an atomic number of from 9 to 35 in the 3- or 4-position, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl, or piperidinyl ring;
$R_3$ is hydrogen and $R_4$ is methoxy;
E is oxygen,
or an acid addition salt thereof.

10. A compound of claim 7 which is $(1\alpha,2\beta,5\beta)$-N-[5-(acetyloxy)-2-(1-pyrrolidinyl)cyclohexyl]-3,4-dichloro-N-methylbenzeneacetamide or a pharmacologically acceptable salt thereof.

11. A compound according to claim 1 wherein p is 1 to 3; n is 1 to 3,
q is 0 or 1;
at least one of X and Y is a halogen having an atomic number of from 9 to 35 in the 3- or 4-positions of the phenyl ring, or both of X and Y are such a halogen in the 3- and 4-positions of the phenyl ring;
R is $C_1$ to $C_3$-alkyl;
each of $R_1$ and $R_2$ is a $C_1$ to $C_3$-alkyl;
$R_3$ and $R_4$ are taken together to be the ring forming group $-ECH_2CH_2E-$, and each E is oxygen,
or a pharmacologically acceptable salt thereof.

12. A compound according to claim 11 which is 4-bromo-N-[7-(dimethylamino)-1,4-dioxaspiro[4.5]dec-8-yl]-N-methylbenzamide, or a pharmacologically acceptable salt thereof.

13. A compound according to claim 11 wherein the compound is trans-3,4-dichloro-N-[7-(dimethylamino)-1,4-dioxaspiro[4.5]dec-8-yl]-N-methylbenzeneacetamide, or a pharmacologically acceptable salt thereof.

14. A compound according to claim 1 wherein p is 1 to 3;
n is 1 to 3;
q is 0 or 1;
at least one of X and Y is a halogen having an atomic number of from 9 to 35 in the 3- or 4-position of the phenyl ring;
R is $C_1$ to $C_3$-alkyl;
each of $R_1$ and $R_2$ is $C_1$ to $C_3$-alkyl;
one of $R_3$ and $R_4$ is hydrogen and the other of $R_3$ and $R_4$ is methoxy;
E is oxygen;
or a pharmacologically acceptable salt thereof.

15. A compound according to claim 9 wherein the compound is 3,4-dichloro-N-[4-methoxy-2-(1-pyrrolidinyl)cyclohexyl]-N-methylbenzeneacetamide, or a pharmacologically acceptable salt thereof.

16. A compound according to claim 1 wherein p is 1 to 3;
n is 1 to 3;
q is 0 or 1;
at least one of X and Y is a halogen having an atomic number of from 9 to 35 in the 3- or 4-position of the phenyl ring;
R is hydrogen;
each of $R_1$ and $R_2$ is a $C_1$ to $C_3$-alkyl;
$R_3$ and $R_4$ are taken together to form the $-ECH^2CH^2E-$ ring forming group, and each E is oxygen;
or a pharmacologically acceptable salt thereof.

17. A compound according to claim 16 where the compound is trans-3,4-dichloro-N-[7-(dimethylamino)-1,4-dioxaspiro[4.5]dec-8-yl]benzeneacetamide.

18. A compound according to claim 1 where the compound is one in which
p is 1 to 3;
n is 1 to 3;
q is 0 or 1;
at least one of X and Y is a halogen having an atomic number of from 9 to 35 in the 3- or 4-position of the phenyl ring;
R is $C_1$ to $C_3$-alkyl;
$R_1$ is allyl;
$R_2$ is $C_1$ to $C_3$-alkyl;
$R_3$ and $R_4$ are taken together to be the ring forming group $-ECH_2CH_2E-$, and each E is oxygen,
or a pharmacologically acceptable salt thereof.

19. A compound according to claim 18 wherein the compound is trans-3,4-dichloro-N-methyl-N-[7-[methyl(2-propenyl)amino]-1,4-dioxaspiro[4.5]dec-8-yl]benzeneacetamide, or a pharmacologically acceptable salt thereof.

20. A composition useful in pharmaceutically effective dosage unit form for alleviating pain in warm blooded mammals which comprises a compound of Formula I in claim 1 in combination with a pharmaceutically acceptable carrier.

21. A method for alleviating pain which comprises administering to an animal suffering pain an effective amount of a compound of Formula I in claim 1 in a pharmaceutical dosage unit form.

22. A compound according to claim 1 wherein the compound is selected from the group consisting of:
4-bromo-N-[8-(dimethylamino)-1,4-dioxaspiro[4.5]dec-7-yl]-N-methylbenzamide,
3,4-dichloro-N-[8-(dimethylamino)-1,4-dioxaspiro[4.5]dec-7-yl]-N-methylbenzamide,
3,4-dichloro-N-[8-(dimethylamino)-1,4-dioxaspiro[4.5]dec-7-yl]-benzeneacetamide,
4-bromo-N-[7-(dimethylamino)-1,4-dioxazpiro[4.5]dec-8-yl]-benzamide,
4-bromo-N-[8-(dimethylamino)-1,4-dioxazpiro[4.5]dec-7-yl]-benazmide,
4-bromo-N-methyl-N-[8-(1-pyrrolidinyl)-1,4-dioxazpiro[5.4]dec-7-yl]benzamide, 4-bromo-N-methyl-N-[7-(1-pyrrolidinyl)-1,4-dioxaspiro[4.5]dec-8-yl]benzamide, 3,4-dichloro-N-[5-(hydroxyimino)-2-(1-pyrrolidinyl)cyclohexyl]-N-methylbenzeneacetamide, 3,4-dichloro-N-methyl-N-[7-(1-pyrrolidinyl)-1,4-dioxaspiro[4.5]-dec-8-yl]benzeneacetamide, 3,4-dichloro-N-methyl-N-[8-(dimethylamino)-1,4-dioxaspiro[4.5]-dec-7-yl]benzeneacetamide, 3,4-dichloro-N-methyl-N-[8-(1-pyrrolidinyl)-1-oxo-4-thiospiro[4.5]dec-7-yl]benzeneacetamide, N-[4-(acetyloxy)-2-(1-pyrrolidinyl)cyclohexyl]-3,4-dichloro-N-methylbenzeneacetamide, or a pharmacologically acceptable salt thereof.

23. A composition of claim 20 wherein the compound of Formula I is a compound of the formula

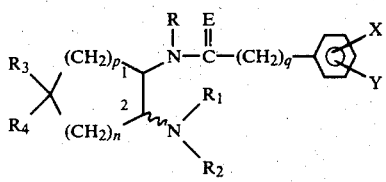

wherein
p is 1 to 3,
n is 1 to 3,
q is 0 or 1;
at least one of X and Y is a halogen having an atomic number of from 9 to 35 in the 3- or 4-position of the phenyl ring, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl or piperidinyl group;
$R_3$ and $R_4$ are taken together to form the ring group —$ECH_2CH_2E$—, and each E is oxygen;
or a pharmacologically acceptable salt thereof.

24. A composition of claim 27 wherein the compound of Formula I is trans-3,4-dichloro-N-methyl-N[7-(1-pyrrolidinyl)-1,4-dioxaspiro[4.5]dec-8-yl]-benzeneacetamide, or a pharmacologically acceptable salt thereof.

25. A method of claim 23 wherein the compound of Formula I in claim 1 is a compound of the formula

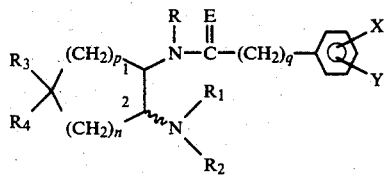

wherein
p is 1 to 3;
n is 1 to 3;
q is 0 or 1;
at least one of X and Y is a halogen having an atomic number of from 9 to 35 in the 3- or 4-position of the phenyl ring, or both of X and Y are such a halogen in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl or piperidinyl group;
$R_3$ and $R_4$ are taken together to form the ring group —$ECH_2CH_2E$—, and each E is oxygen;
or a pharmacologically acceptable salt thereof.

26. A method of claim 29 wherein the compound is trans-3,4-dichloro-N-methyl-N-[7-(1-pyrrolidinyl)-1,4-dioxaspiro[4.5]dec-8-yl]benzeneacetamide or a pharmacologically acceptable salt thereof.

* * * * *

UNITED STATES PATENT OFFICE
CERTIFICATE OF CORRECTION

Patent No. 4,360,531              Dated November 23, 1982

Inventor(s) Moses W. McMillan and Jacob Szmuszkovicz

It is certified that error appears in the above-identified patent and that said Letters Patent are hereby corrected as shown below:

Column 2, line 20: "trans3,4-" should read -- trans- 3,4- --.
Column 4, line 15: "third ring" should read -- third substituted ring --.
Column 8, line 23: "imidazoles (II)" should read -- imidazoles (III) --.
Column 9, Chart A, Formula XII, item (1) (3 occurrences): "CH$_2$SO$_2$Cl" should read -- CH$_3$SO$_2$Cl --.
Column 13, Chart B, Formula XVII should appear as follows instead of as in the patent:

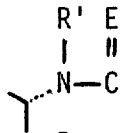

Column 24, line 3: "['.1.0]" should read -- [4.1.0] --.
Column 30, line 35: "N$^+$=CHCH=CH" should read -- N̊=CHCH=C --.
Column 31, line 15: "HN$^+$," should read --(H̊N, --.
Column 31, line 17: "((CH$_3$)$_2$N$^+$" should read -- ((CH$_3$)$_2$N̊ --.
Column 31, line 26: "(N$^+$H," should read -- (NH̊, --.
Column 32, line 12: "trans3,4-" should read -- trans-3,4- --.
Column 32, line 40: "((CH$_3$)$_2$N$^+$" should read -- ((CH$_3$)$_2$N̊ --.
Column 33, line 16: "((CH$_3$)$_2$N$^+$" should read -- ((CH$_3$)$_2$N̊ --.
Column 33, line 57: "2.0 l" should read --2.0 ℓ --.
Column 34, lines 8-9: "propenyl-)amino" should read -- propenyl)-amino --.
Column 34, lines 12-13: "propenyl-)amino" should read -- propenyl)amino --.
Column 34, line 34: "C=O$_+$" should read -- C=O̊ --.
Column 40, line 20: "monohydrichloride" should read -- monohydrochloride --.
Column 41, line 2: "pl q.4" should read -- q.4 --(omit pl - q.4 belongs out at left margin in line with item p).
Column 41, line 6: "pentyl]-methyl" should read -- pentyl]-N-methyl --.

UNITED STATES PATENT OFFICE

CERTIFICATE OF CORRECTION

Patent No. 4,360,531　　　　　　　　　　Dated　November 23, 1982

Inventor(s) Moses W. McMillan and Jacob Szmuszkovicz

It is certified that error appears in the above-identified patent and that said Letters Patent are hereby corrected as shown below:

Column 46, Claim 24, line 4: "claim 27" should read -- claim 23 --.
Column 46, Claim 25, line 9: "claim 23" should read -- claim 21 --.
Column 46, Claim 26, line 35: "claim 29" should read -- claim 25 --.

Signed and Sealed this

Twenty-third Day of August 1983

[SEAL]

Attest:

GERALD J. MOSSINGHOFF

Attesting Officer　　　Commissioner of Patents and Trademarks